US012624090B2

(12) United States Patent
Chen et al.

(10) Patent No.: US 12,624,090 B2
(45) Date of Patent: May 12, 2026

(54) METHOD AND ANTIBODY FOR DETECTION OF HBcAg

(71) Applicants: Xiamen Innodx Biotech Co., Ltd, Xiamen (CN); Xiamen University, Xiamen (CN)

(72) Inventors: Zimin Chen, Xiamen (CN); Junhui Xiong, Xiamen (CN); Jiaqi Liu, Xiamen (CN); Shaojuan Wang, Xiamen (CN); Shengxiang Ge, Xiamen (CN); Quan Yuan, Xiamen (CN); Liuwei Song, Xiamen (CN); Xudong Sun, Xiamen (CN)

(73) Assignees: XIAMEN INNODX BIOTECH CO., LTD, Xiamen (CN); XIAMEN UNIVERSITY, Xiamen (CN)

( * ) Notice: Subject to any disclaimer, the term of this patent is extended or adjusted under 35 U.S.C. 154(b) by 915 days.

(21) Appl. No.: 17/791,415

(22) PCT Filed: Jan. 18, 2021

(86) PCT No.: PCT/CN2021/072483
§ 371 (c)(1),
(2) Date: Jul. 7, 2022

(87) PCT Pub. No.: WO2021/143902
PCT Pub. Date: Jul. 22, 2021

(65) Prior Publication Data
US 2023/0069418 A1 Mar. 2, 2023

(30) Foreign Application Priority Data
Jan. 19, 2020 (CN) ........................ 202010059190.X

(51) Int. Cl.
*C07K 16/082* (2026.01)
(52) U.S. Cl.
CPC ........ *C07K 16/082* (2013.01); *C07K 2317/24* (2013.01); *C07K 2317/56* (2013.01)
(58) Field of Classification Search
CPC ............. C07K 16/082; G01N 2469/10; G01N 33/5762; G01N 2333/02; G01N 33/577; G01N 33/536; G01N 33/56983
See application file for complete search history.

(56) References Cited

U.S. PATENT DOCUMENTS 5,726,011 A 3/1998 Milich et al.
2006/0008798 A1 1/2006 Chien et al.

| 2010/0074901 | A1 | 3/2010 | Mercken et al. |
| 2012/0308580 | A1 | 12/2012 | Bertoletti et al. |
| 2015/0246948 | A1 | 9/2015 | Yuan et al. |
| 2016/0122420 | A1 | 5/2016 | Rowlands et al. |
| 2019/0023775 | A1 | 1/2019 | Bachman et al. |

FOREIGN PATENT DOCUMENTS

| CN | 1869701 | A | 11/2006 | |
| CN | 102762220 | A | 10/2012 | |
| CN | 102781961 | A | 11/2012 | |
| CN | 103483421 | A | 1/2014 | |
| CN | 105431457 | A | 3/2016 | |
| CN | 106046155 | A | 10/2016 | |
| CN | 109336973 | A | 2/2019 | |
| JP | 2015522563 | A | 8/2015 | |
| JP | 2017515508 | A | 6/2017 | |
| WO | WO 02/14871 | A1 | 2/2002 | |
| WO | WO 2004/022585 | A1 | 3/2004 | |
| WO | WO 2008/003236 | A1 | 1/2008 | |
| WO | WO-2017148432 | A1 * | 9/2017 | ............. C12N 15/11 |
| WO | WO 2019/018629 | A1 | 1/2019 | |
| WO | WO 2019/099624 | A1 | 5/2019 | |
| WO | WO 2019/226699 | A1 | 11/2019 | |
| WO | WO 2022/012539 | A1 | 1/2022 | |

OTHER PUBLICATIONS

Almagro & Fransson, Frontiers in Bioscience 2008; 13:1619-33 (Year: 2008).*
Hlozanek et al., "Monoclonal Antibodies against Genetically Manipulated Hepatitis B Core Antigen", Folia Biologica (Praha), 1987, 33: 295-300.
Missale et al., "HLA-A31- and HLA-Aw68-restricted Cytotoxic T Cell Responses to a Single Hepatitis B Virus Nucleocapsid Epitope during Acute Viral Hepatitis", Journal of Experimental Medicine, 1993, 177: 751-762.
Pushko et al., "Identification of Hepatitis B Virus Core Protein Regions Exposed or Internalized at the Surface of HBcAg Particles by Scanning with Monoclonal Antibodies", Virology, 1994, 202: 912-920.
Tedder et al., "Production of monoclonal antibodies to hepatitis B surface and core antigens, and use in the detection of viral antigens in liver biopsies", The Journal of Hygiene, 1983, 90: 135-142.

(Continued)

*Primary Examiner* — Peter J Reddig
(74) *Attorney, Agent, or Firm* — James S. Keddie; Bozicevic, Field & Francis LLP

(57) ABSTRACT

In the field of Hepatitis B virus (HBV) detection, disclosed are a method for detecting HBcAg by means of using a double antibody sandwich method, and an antibody and kit for detecting HBcAg; also included is a monoclonal antibody that can be used in the immunological detection of HBcAg in a tissue or cell sample.

19 Claims, 3 Drawing Sheets

Specification includes a Sequence Listing.

(56) References Cited

OTHER PUBLICATIONS

Ueno et al., "Production of Monoclonal Antibodies against Recombinant HBcAg", The Tohoku Journal of Experimental Medicine, 1990, 161: 253-255.

Wang et al., "Specific determination of hepatitis B e antigen by antibodies targeting precorefacilitates clinical diagnosis and drug evaluation against hepatitis B virus infection", Emerging Microbes & Infections, Jan. 1, 2021, 10(1): 37-50.

Zhang et al., "Chimeric rabbit/human Fab antibodies against the hepatitis B e-antigen and their potential applications in assays, characterization, and therapy", J. Biol. Chem., 2017, 292(40): 16760-16772.

Putnam et al., "Sea Anemone Genome Reveals Ancestral Eumetazoan Gene Repertoire and Genomic Organization", Science, 2007, 317: 86-94.

* cited by examiner

HepG2-N10

HepG2

Commercial polyclonal antibody

2A7 Monoclonal antibody

C57BL/6

HBV-TG

SEQUENCE LISTING

```
<160> NUMBER OF SEQ ID NOS: 50

<210> SEQ ID NO 1
<211> LENGTH: 114
<212> TYPE: PRT
<213> ORGANISM: Artificial sequence
<220> FEATURE:
<223> OTHER INFORMATION: 18B2-2 VH

<400> SEQUENCE: 1

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ala Phe Thr Asp Tyr
            20                  25                  30

Pro Val His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Ala Ser Ala Asn Thr Ala Tyr
65                  70                  75                  80

Leu Gln Ile Asn Asn Leu Lys Asn Glu Asp Thr Ala Thr Tyr Phe Cys
                85                  90                  95

Asp His Tyr Ser Met Asp Tyr Trp Gly Gln Gly Thr Ser Val Thr Val
            100                 105                 110

Ser Ser

<210> SEQ ID NO 2
<211> LENGTH: 112
<212> TYPE: PRT
<213> ORGANISM: Artificial sequence
<220> FEATURE:
<223> OTHER INFORMATION: 18B2-2 VL

<400> SEQUENCE: 2

Asp Ile Val Ile Thr Gln Asp Glu Leu Ser Asn Pro Val Thr Ser Gly
1               5                   10                  15

Glu Ser Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
                85                  90                  95

Val Glu Tyr Pro Phe Thr Phe Gly Ser Gly Thr Lys Leu Glu Ile Lys
            100                 105                 110

<210> SEQ ID NO 3
<211> LENGTH: 8
<212> TYPE: PRT
<213> ORGANISM: Artificial sequence
<220> FEATURE:
```

<223> OTHER INFORMATION: 18B2-2 HCDR1

<400> SEQUENCE: 3

Gly Tyr Ala Phe Thr Asp Tyr Pro
1               5

<210> SEQ ID NO 4
<211> LENGTH: 8
<212> TYPE: PRT
<213> ORGANISM: Artificial sequence
<220> FEATURE:
<223> OTHER INFORMATION: 18B2-2 HCDR2

<400> SEQUENCE: 4

Ile Asn Thr Glu Thr Gly Glu Pro
1               5

<210> SEQ ID NO 5
<211> LENGTH: 7
<212> TYPE: PRT
<213> ORGANISM: Artificial sequence
<220> FEATURE:
<223> OTHER INFORMATION: 18B2-2 HCDR3

<400> SEQUENCE: 5

Asp His Tyr Ser Met Asp Tyr
1               5

<210> SEQ ID NO 6
<211> LENGTH: 11
<212> TYPE: PRT
<213> ORGANISM: Artificial sequence
<220> FEATURE:
<223> OTHER INFORMATION: 18B2-2 LCDR1

<400> SEQUENCE: 6

Lys Ser Leu Leu Tyr Lys Asp Gly Lys Thr Tyr
1               5                   10

<210> SEQ ID NO 7
<211> LENGTH: 3
<212> TYPE: PRT
<213> ORGANISM: Artificial sequence
<220> FEATURE:
<223> OTHER INFORMATION: 18B2-2 LCDR2

<400> SEQUENCE: 7

Leu Met Ser
1

<210> SEQ ID NO 8
<211> LENGTH: 9
<212> TYPE: PRT
<213> ORGANISM: Artificial sequence
<220> FEATURE:
<223> OTHER INFORMATION: 18B2-2 LCDR3

<400> SEQUENCE: 8

Gln Gln Leu Val Glu Tyr Pro Phe Thr
1               5

<210> SEQ ID NO 9
<211> LENGTH: 122
<212> TYPE: PRT
<213> ORGANISM: Artificial sequence
<220> FEATURE:
<223> OTHER INFORMATION: 2A7 VH

<400> SEQUENCE: 9

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Arg Tyr
            20                  25                  30

Trp Met His Trp Val Met Gln Arg Pro Gly Gln Asp Leu Glu Trp Ile
        35                  40                  45

Gly Glu Ile Asn Pro Ile Asn Gly Arg Thr Asn Tyr Asn Glu Lys Phe
    50                  55                  60

Arg Arg Lys Ala Thr Leu Thr Val Asp Lys Ser Ser Ser Thr Val Tyr
65                  70                  75                  80

Ile Gln Phe Ser Ser Leu Thr Ser Glu Asp Ser Ala Val Tyr Phe Cys
                85                  90                  95

Thr Arg Glu Gly Tyr Arg Asn Asp Tyr Tyr Ala Met Asp Phe Trp
            100                 105                 110

Gly Arg Gly Thr Ser Val Thr Val Ser Ser
        115                 120

<210> SEQ ID NO 10
<211> LENGTH: 107
<212> TYPE: PRT
<213> ORGANISM: Artificial sequence
<220> FEATURE:
<223> OTHER INFORMATION: 2A7 VL

<400> SEQUENCE: 10

Asp Ile Gln Met Thr Gln Thr Ser Ser Ser Leu Ser Ala Ser Pro Gly
1               5                   10                  15

Asp Arg Val Thr Ile Ser Cys Arg Ala Ser Gln Gly Ile Asn Asn Tyr
            20                  25                  30

Leu Asn Trp Tyr Lys Gln Lys Thr Asp Gly Thr Phe Lys Leu Leu Ile
        35                  40                  45

Tyr Tyr Thr Ser Tyr Leu His Ser Gly Val Pro Ser Arg Phe Ser Gly
    50                  55                  60

Arg Gly Ser Gly Thr Asp Tyr Ser Leu Thr Ile Ser Asn Leu Glu Pro
65                  70                  75                  80

Glu Asp Val Ala Thr Tyr Tyr Cys Gln Gln Tyr Gly Lys Leu Pro Trp
                85                  90                  95

Thr Phe Gly Gly Gly Thr Lys Leu Glu Ile Lys
            100                 105

<210> SEQ ID NO 11
<211> LENGTH: 8
<212> TYPE: PRT
<213> ORGANISM: Artificial sequence
<220> FEATURE:
<223> OTHER INFORMATION: 2A7 HCDR1

<400> SEQUENCE: 11

Gly Tyr Thr Phe Thr Arg Tyr Trp
1               5

<210> SEQ ID NO 12
<211> LENGTH: 8
<212> TYPE: PRT
<213> ORGANISM: Artificial sequence
<220> FEATURE:
<223> OTHER INFORMATION: 2A7 HCDR2

-continued

```
<400> SEQUENCE: 12

Ile Asn Pro Ile Asn Gly Arg Thr
1               5

<210> SEQ ID NO 13
<211> LENGTH: 15
<212> TYPE: PRT
<213> ORGANISM: Artificial sequence
<220> FEATURE:
<223> OTHER INFORMATION: 2A7 HCDR3

<400> SEQUENCE: 13

Thr Arg Glu Gly Tyr Arg Asn Asp Tyr Tyr Tyr Ala Met Asp Phe
1               5                   10              15

<210> SEQ ID NO 14
<211> LENGTH: 6
<212> TYPE: PRT
<213> ORGANISM: Artificial sequence
<220> FEATURE:
<223> OTHER INFORMATION: 2A7 LCDR1

<400> SEQUENCE: 14

Gln Gly Ile Asn Asn Tyr
1               5

<210> SEQ ID NO 15
<211> LENGTH: 3
<212> TYPE: PRT
<213> ORGANISM: Artificial sequence
<220> FEATURE:
<223> OTHER INFORMATION: 2A7 LCDR2

<400> SEQUENCE: 15

Tyr Thr Ser
1

<210> SEQ ID NO 16
<211> LENGTH: 9
<212> TYPE: PRT
<213> ORGANISM: Artificial sequence
<220> FEATURE:
<223> OTHER INFORMATION: 2A7 LCDR3

<400> SEQUENCE: 16

Gln Gln Tyr Gly Lys Leu Pro Trp Thr
1               5

<210> SEQ ID NO 17
<211> LENGTH: 183
<212> TYPE: PRT
<213> ORGANISM: Artificial sequence
<220> FEATURE:
<223> OTHER INFORMATION: C183

<400> SEQUENCE: 17

Met Asp Ile Asp Pro Tyr Lys Glu Phe Gly Ala Ser Val Glu Leu Leu
1               5                   10              15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60
```

```
Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
        130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 18
<211> LENGTH: 15
<212> TYPE: PRT
<213> ORGANISM: Artificial Sequence
<220> FEATURE:
<223> OTHER INFORMATION: S1

<400> SEQUENCE: 18

Met Asp Ile Asp Pro Tyr Lys Glu Phe Gly Ala Thr Val Glu Leu
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: S2

<400> SEQUENCE: 19

Tyr Lys Glu Phe Gly Ala Thr Val Glu Leu Leu Ser Phe Leu Pro
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: S3

<400> SEQUENCE: 20

Ala Thr Val Glu Leu Leu Ser Phe Leu Pro Ser Asp Phe Phe Pro
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: S4

<400> SEQUENCE: 21

Leu Ser Phe Leu Pro Ser Asp Phe Phe Pro Ser Ile Arg Asp Leu
1               5                   10                  15

<210> SEQ ID NO 22
<211> LENGTH: 15
```

```
<212> TYPE: PRT
<213> ORGANISM: Artificial Sequence
<220> FEATURE:
<223> OTHER INFORMATION: S5

<400> SEQUENCE: 22

Ser Asp Phe Phe Pro Ser Val Arg Asp Leu Leu Asp Thr Ala Ser
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: S6

<400> SEQUENCE: 23

Ser Val Arg Asp Leu Leu Asp Thr Ala Ser Ala Leu Tyr Arg Glu
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: S7

<400> SEQUENCE: 24

Leu Asp Thr Ala Ser Ala Leu Tyr Arg Glu Ala Leu Glu Ser Pro
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: S8

<400> SEQUENCE: 25

Ala Leu Tyr Arg Glu Ala Leu Glu Ser Pro Glu His Cys Ser Pro
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: S9

<400> SEQUENCE: 26

Ala Leu Glu Ser Pro Glu His Cys Ser Pro His His Thr Ala Leu
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: S10

<400> SEQUENCE: 27

Glu His Cys Ser Pro His His Thr Ala Leu Arg Gln Ala Ile Leu
1               5                   10                  15

<210> SEQ ID NO 28
<211> LENGTH: 15
<212> TYPE: PRT
```

```
<213> ORGANISM: Artificial Sequence
<220> FEATURE:
<223> OTHER INFORMATION: S11

<400> SEQUENCE: 28

His His Thr Ala Leu Arg Gln Ala Ile Leu Cys Trp Gly Glu Leu
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: S12

<400> SEQUENCE: 29

Arg Gln Ala Ile Leu Cys Trp Gly Glu Leu Met Asn Leu Ala Thr
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: S13

<400> SEQUENCE: 30

Cys Trp Gly Glu Leu Met Thr Leu Ala Thr Trp Val Gly Val Asn
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: S14

<400> SEQUENCE: 31

Met Thr Leu Ala Thr Trp Val Gly Val Asn Leu Glu Asp Pro Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: S15

<400> SEQUENCE: 32

Trp Val Gly Val Asn Leu Glu Asp Pro Ala Ser Arg Asp Leu Val
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: S16

<400> SEQUENCE: 33

Leu Glu Asp Pro Ala Ser Arg Asp Leu Val Val Ser Tyr Val Asn
1               5                   10                  15

<210> SEQ ID NO 34
<211> LENGTH: 15
<212> TYPE: PRT
<213> ORGANISM: Artificial Sequence
```

```
<220> FEATURE:
<223> OTHER INFORMATION: S17

<400> SEQUENCE: 34

Ser Arg Asp Leu Val Val Ser Tyr Val Asn Thr Asn Met Gly Leu
1               5               10              15

<210> SEQ ID NO 35
<211> LENGTH: 15
<212> TYPE: PRT
<213> ORGANISM: Artificial Sequence
<220> FEATURE:
<223> OTHER INFORMATION: S18

<400> SEQUENCE: 35

Val Ser Tyr Val Asn Thr Asn Met Gly Leu Lys Phe Arg Gln Leu
1               5               10              15

<210> SEQ ID NO 36
<211> LENGTH: 15
<212> TYPE: PRT
<213> ORGANISM: Artificial Sequence
<220> FEATURE:
<223> OTHER INFORMATION: S19

<400> SEQUENCE: 36

Thr Asn Met Gly Leu Lys Phe Arg Gln Leu Leu Trp Phe His Ile
1               5               10              15

<210> SEQ ID NO 37
<211> LENGTH: 15
<212> TYPE: PRT
<213> ORGANISM: Artificial Sequence
<220> FEATURE:
<223> OTHER INFORMATION: S20

<400> SEQUENCE: 37

Lys Phe Arg Gln Leu Leu Trp Phe His Ile Ser Cys Leu Thr Phe
1               5               10              15

<210> SEQ ID NO 38
<211> LENGTH: 15
<212> TYPE: PRT
<213> ORGANISM: Artificial Sequence
<220> FEATURE:
<223> OTHER INFORMATION: S21

<400> SEQUENCE: 38

Leu Trp Phe His Ile Ser Cys Leu Thr Phe Gly Arg Glu Thr Val
1               5               10              15

<210> SEQ ID NO 39
<211> LENGTH: 15
<212> TYPE: PRT
<213> ORGANISM: Artificial Sequence
<220> FEATURE:
<223> OTHER INFORMATION: S22

<400> SEQUENCE: 39

Ser Cys Leu Thr Phe Gly Arg Glu Thr Val Ile Glu Tyr Leu Val
1               5               10              15

<210> SEQ ID NO 40
<211> LENGTH: 15
<212> TYPE: PRT
<213> ORGANISM: Artificial Sequence
<220> FEATURE:
```

-continued

```
<223> OTHER INFORMATION: S23

<400> SEQUENCE: 40

Gly Arg Glu Thr Val Ile Glu Tyr Leu Val Ser Phe Gly Val Trp
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: S24

<400> SEQUENCE: 41

Ile Glu Tyr Leu Val Ser Phe Gly Val Trp Ile Arg Thr Pro Pro
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: S25

<400> SEQUENCE: 42

Ser Phe Gly Val Trp Ile Arg Thr Pro Pro Ala Tyr Arg Pro Pro
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: S26

<400> SEQUENCE: 43

Ile Arg Thr Pro Pro Ala Tyr Arg Pro Pro Asn Ala Pro Ile Leu
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: S27

<400> SEQUENCE: 44

Ala Tyr Arg Pro Pro Asn Ala Pro Ile Leu Ser Thr Leu Pro Glu
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: S28

<400> SEQUENCE: 45

Asn Ala Pro Ile Leu Ser Thr Leu Pro Glu Thr Thr Val Val Arg
1               5                   10                  15

<210> SEQ ID NO 46
<211> LENGTH: 14
<212> TYPE: PRT
<213> ORGANISM: Artificial Sequence
<220> FEATURE:
<223> OTHER INFORMATION: S29
```

<400> SEQUENCE: 46

Ser Thr Leu Pro Glu Thr Thr Val Val Arg Arg Arg Gly Arg
1               5                   10

<210> SEQ ID NO 47
<211> LENGTH: 12
<212> TYPE: PRT
<213> ORGANISM: Artificial Sequence
<220> FEATURE:
<223> OTHER INFORMATION: S30

<400> SEQUENCE: 47

Ser Thr Leu Pro Glu Thr Thr Val Val Arg Arg Arg
1               5                   10

<210> SEQ ID NO 48
<211> LENGTH: 34
<212> TYPE: PRT
<213> ORGANISM: Artificial Sequence
<220> FEATURE:
<223> OTHER INFORMATION: S31

<400> SEQUENCE: 48

Arg Arg Arg Gly Arg Ser Pro Arg Arg Arg Thr Pro Ser Pro Arg Arg
1               5                   10                  15

Arg Arg Ser Gln Ser Pro Arg Arg Arg Ser Gln Ser Arg Glu Ser
            20                  25                  30

Gln Cys

<210> SEQ ID NO 49
<211> LENGTH: 212
<212> TYPE: PRT
<213> ORGANISM: Artificial Sequence
<220> FEATURE:
<223> OTHER INFORMATION: Amino acid sequence consisting of HBcAg
      sequence of HBV gene and the sequence from -29 to -1 at its
      N-terminal

<400> SEQUENCE: 49

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Ser Val Glu Leu Leu Ser Phe Leu
        35                  40                  45

Pro Ser Asp Phe Phe Pro Ser Ile Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Asn
                85                  90                  95

Leu Ala Thr Trp Val Gly Ser Asn Leu Glu Asp Pro Ala Ser Arg Glu
                100                 105                 110

Leu Val Val Ser Tyr Val Asn Val Asn Met Gly Leu Lys Ile Arg Gln
            115                 120                 125

Leu Leu Trp Phe His Ile Ser Cys Leu Thr Phe Gly Arg Glu Thr Val
        130                 135                 140

Leu Glu Tyr Leu Val Ser Phe Gly Val Trp Ile Arg Thr Pro Pro Ala
145                 150                 155                 160

-continued

```
Tyr Arg Pro Pro Asn Ala Pro Ile Leu Ser Thr Leu Pro Glu Thr Thr
                165                 170             175

Val Val Arg Arg Arg Gly Arg Ser Pro Arg Arg Arg Thr Pro Ser Pro
            180                 185             190

Arg Arg Arg Arg Ser Gln Ser Pro Arg Arg Arg Arg Ser Gln Ser Arg
        195                 200                 205

Glu Ser Gln Cys
    210

<210> SEQ ID NO 50
<211> LENGTH: 5
<212> TYPE: PRT
<213> ORGANISM: Artificial Sequence
<220> FEATURE:
<223> OTHER INFORMATION: Linker

<400> SEQUENCE: 50

Gly Gly Gly Gly Ser
1               5
```

METHOD AND ANTIBODY FOR DETECTION OF HBcAg

CROSS-REFERENCE TO RELATED APPLICATION

The application is a § 371 national phase of International Application No. PCT/CN2021/072483, filed on Jan. 18, 2021, which claims priority to Chinese Application No. 202010059190.X, filed Jan. 19, 2020, the entire contents of both applications are hereby incorporated by reference.

Incorporation by Reference of Sequence Listing Provided as a Text File

A Sequence Listing is provided herewith in a text file entitled IEC200405PUS_ST25.txt, created on Aug. 26, 2025, and having a size of 17,678 bytes. The contents of this text file are incorporated herein by reference in its entirety.

TECHNICAL FIELD

The present invention relates to the field of hepatitis B virus (HBV) detection. Specifically, the present invention provides a method for the detection of HBcAg by using a double-antibody sandwich method, as well as an antibody and kit used for the detection. The present invention also provides a monoclonal antibody that can be used for HBcAg immunological detection of tissue or cell samples.

BACKGROUND ART

Hepatitis B virus infection, especially chronic HBV infection, is one of the most important public health problems worldwide (Dienstag J L. Hepatitis B virus infection. N Engl J Med 2008 Oct. 2; 359(14):1486-1500).

At present, HBV serum markers (such as the Hepatitis B serologic test of HBsAg, HBsAb, HBeAg, HBeAb, HBcAb) are widely used as the routine detection standard for current HBV infection and past HBV infection. However, the high mutation rate combined with the huge number of HBV carriers leads to a high incidence of false negatives in the conventional Hepatitis B serologic test of HBsAg, HBsAb, HBeAg, HBeAb and HBcAb. In addition, the Hepatitis B serologic test of HBsAg, HBsAb, HBeAg, HBeAb and HBcAb cannot quantitatively reflect the degree of virus replication and infectivity, often have results that are suspicious and difficult to explain, and also cannot directly determine whether the tested individuals are not infected with HBV.

HBV DNA is a direct indicator of HBV replication, and its dot blot test (or PCR test) is the gold standard for judging infection and infectivity in hepatitis B patients and HBV carriers. Both PCR test and dot blot test can be used as direct indicators of HBV infection and infectivity, but they are not suitable for large-scale screening and routine use.

Among all serum marker antigens (HBV PreS1, HBcAg, HBxAg, DNAP, HBV PreS2, etc.) that may be highly related to HBV DNA, HBcAg has always been considered to be an antigen directly related to HBV DNA, and the detection of HBcAg has unique significance in quantification of replicative viruses and diagnosis of HBsAg-negative HBV-infected patients and HBV patients. At present, there is no specific HBcAg detection reagent developed in the market. The HBcAg immunodiagnostic reagents that have been reported or have been developed usually adopt the pre-treatment of sample before detection (lysing virus, rupturing membrane and inactivating HBcAb) or detection of HBcAg-HBcAb immune complex; however, the former method has complex procedures and is not easy to be accepted by clinical customers, and is not suitable for large-scale screening of blood donors and epidemiological investigations, while the latter method is difficult to achieve the ideal specificity and sensitivity due to the particularity of the detection method. In 2006, it was reported in the patent "Method and diagnostic kit for combined detection of hepatitis B virus pre-S1 antigen and core antigen" that virus particles were captured by using sAg antibody followed by membrane rupture, lysis of virus and detection of cAg in core particle for HBcAg detection, but its sensitivity was unsatisfactory.

It has urgent practical significance in evaluation of antiviral efficacy and prognosis of HBV patients to develop a simple, accurate and highly sensitive HBcAg luminescent detection reagent.

Contents of the Present Invention

After extensive experimental research, the inventors unexpectedly found a pair of antibodies that bind to specific epitopes, which is particularly suitable for the detection of HBcAg by double-antibody sandwich method. On this basis, the inventors developed a new HBcAg quantitative detection kit and detection method. The detection method reaches a level of sensitivity comparable to that of DNA method and realizes rapid and high-throughput detection, and thus has great clinical application value.

Kit

Therefore, in a first aspect, the present invention provides a kit, which comprises:

(i) a first antibody, an isolated nucleic acid molecule encoding the first antibody, a vector comprising the isolated nucleic acid molecule, or a recombinant cell expressing the first antibody; wherein the first antibody is selected from an antibody or antigen-binding fragment thereof that is capable of specifically binding to an epitope contained in positions 150-183 of HBcAg protein; and, (ii) a second antibody, an isolated nucleic acid molecule encoding the second antibody, a vector comprising the isolated nucleic acid molecule, or a recombinant cell expressing the second antibody; wherein the second antibody is selected from an antibody or antigen-binding fragment thereof that is capable of specifically binding to an epitope contained in positions 141-154 of HBcAg protein.

Herein, the expression "epitope contained in positions 150-183 of HBcAg protein" or similar expressions means that the epitope is present within or overlapping the amino acids 150-183 of the HBcAg protein. In other words, the antibody or antigen-binding fragment thereof that is capable of specifically binding to an epitope contained in positions 150 to 183 of HBcAg protein is an antibody or antigen-binding fragment thereof that is capable of specifically binding to the amino acids 150 to 183 of HBcAg protein or fragment thereof.

In certain exemplary embodiments, the HBcAg protein has a sequence set forth in SEQ ID NO:17.

In certain embodiments, the second antibody is selected from an antibody or antigen-binding fragment thereof that is capable of specifically binding an epitope contained in positions 141-152 of HBcAg protein.

In certain embodiments, the first antibody is selected from the following antibody or antigen-binding fragment thereof:

(i) an antibody or antigen-binding fragment thereof, which comprises: a heavy chain variable region (VH) comprising the following 3 complementarity determining regions (CDRs): HCDR1 having a sequence set forth in SEQ ID NO: 3, HCDR2 having a sequence set forth in SEQ ID NO: 4, and HCDR3 having a sequence set forth in SEQ ID NO: 5; and/or, a light chain variable region (VL) comprising the following 3 complementarity determining regions (CDRs): LCDR1 having a sequence set forth in SEQ ID NO: 6, LCDR2 having a sequence set forth in SEQ ID NO: 7, and LCDR3 having a sequence set forth in SEQ ID NO: 8; or, (ii) an antibody or antigen-binding fragment thereof, which comprises: a heavy chain variable region (VH) comprising 3 CDRs contained in the heavy chain variable region set forth in SEQ ID NO: 1; and/or, a light chain variable region (VL) comprising 3 CDRs contained in the light chain variable region set forth in SED ID NO: 2; preferably, the 3 CDRs contained in the heavy chain variable region, and/or the 3 CDRs contained in the light chain variable region are defined by the Kabat, Chothia or IMGT numbering system; or, (iii) an antibody or antigen-binding fragment thereof, in which the antibody is a monoclonal antibody produced by a hybridoma cell line 18B2-2 which is deposited in the China Center for Type Culture Collection (CCTCC) and has the deposit number of CCTCC NO. C2019303.

In certain embodiments, the first antibody comprises:

(a) a heavy chain variable region (VH), which comprises an amino acid sequence selected from the group consisting of: (i) a sequence set forth in SEQ ID NO: 1; (ii) a sequence having a substitution, deletion or addition of one or several amino acids (e.g., substitution, deletion or addition of 1, 2, 3, 4 or 5 amino acids) as compared with the sequence set forth in SEQ ID NO: 1; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence set forth in SEQ ID NO: 1;

and/or, (b) a light chain variable region (VL), which comprises an amino acid sequence selected from the group consisting of: (iv) a sequence set forth in SEQ ID NO: 2; (v) a sequence having a substitution, deletion or addition of one or several amino acids (e.g., substitution, deletion or addition of 1, 2, 3, 4 or 5 amino acids) as compared with the sequence set forth in SEQ ID NO: 2; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence set forth in SEQ ID NO: 2.

In certain embodiments, the substitution as described in (ii) or (v) is a conservative substitution.

In certain embodiments, the first antibody comprises: a VH having the sequence set forth in SEQ ID NO:1 and a VL having the sequence set forth in SEQ ID NO:2.

In certain embodiments, the second antibody is selected from the following antibody or antigen-binding fragment thereof:

(i) an antibody or antigen-binding fragment thereof, which comprises: a heavy chain variable region (VH) comprising the following 3 complementarity determining regions (CDRs): HCDR1 having a sequence set forth in SEQ ID NO: 11, HCDR2 having a sequence set forth in SEQ ID NO: 12, and HCDR3 having a sequence set forth in SEQ ID NO: 13; and/or, a light chain variable region (VL) comprising the following 3 complementarity determining regions (CDRs): LCDR1 having a sequence set forth in SEQ ID NO: 14, LCDR2 having a sequence set forth in SEQ ID NO: 15, and LCDR3 having a sequence set forth in SEQ ID NO: 16; or, (ii) an antibody or antigen-binding fragment thereof, which comprises: a heavy chain variable region (VH) comprising 3 CDRs contained in a heavy chain variable region set forth in SEQ ID NO: 9; and/or, a light chain variable region (VL) comprising 3 CDRs contained in a light chain variable region set forth in SEQ ID NO: 10; preferably, the 3 CDRs contained in the heavy chain variable region, and/or the 3 CDRs contained in the light chain variable region are defined by the Kabat, Chothia or IMGT numbering system; or, (iii) an antibody or antigen-binding fragment thereof, in which the antibody is a monoclonal antibody produced by a hybridoma cell line 2A7 which is deposited in the China Center for Type Culture Collection (CCTCC) and has the deposit number of CCTCC NO. C2019302.

In certain embodiments, the second antibody comprises:

(a) a heavy chain variable region (VH), which comprises an amino acid sequence selected from the group consisting of: (i) a sequence set forth in SEQ ID NO: 9; (ii) a sequence having a substitution, deletion or addition of one or several amino acids (e.g., substitution, deletion or addition of 1, 2, 3, 4 or 5 amino acids) as compared with the sequence set forth in SEQ ID NO: 9; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence set forth in SEQ ID NO: 9; and/or, (b) a light chain variable region (VL), which comprises an amino acid sequence selected from the group consisting of: (iv) a sequence set forth in SEQ ID NO: 10; (v) a sequence having a substitution, deletion or addition of one or several amino acids (e.g., substitution, deletion or addition of 1, 2, 3, 4 or 5 amino acids) as compared with the sequence set forth in SEQ ID NO: 10; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence set forth in SEQ ID NO: 10.

In certain embodiments, the substitution as described in (ii) or (v) is a conservative substitution.

In certain embodiments, the second antibody comprises: a VH having the sequence set forth in SEQ ID NO:9 and a VL having the sequence set forth in SEQ ID NO:10.

In certain embodiments, the first antibody and/or the second antibody comprises a heavy chain constant region (CH) and a light chain constant region (CL).

In certain embodiments, the first antibody and/or the second antibody comprises a mouse heavy chain constant region and a mouse light chain constant region.

In certain embodiments, the first antibody and/or the second antibody is an IgG, IgM, IgE, IgD or IgA antibody. In certain embodiments, the first antibody and/or the second antibody is an IgG antibody.

In certain embodiments, the antigen-binding fragment is selected from the group consisting of Fab, Fab', (Fab')$_2$, Fv, disulfide-linked Fv, scFv, diabody, and single domain antibody (sdAb).

In certain embodiments, the antibody is a murine antibody, chimeric antibody, or humanized antibody.

In some embodiments, the second antibody bears a detectable label.

In other embodiments, the kit further comprises a third antibody capable of specifically binding to the second antibody, and the third antibody bears a detectable label.

As used herein, the detectable label may be any substance detectable by fluorescent, spectroscopic, photochemical, biochemical, immunological, electrical, optical or chemical means. It is particularly preferred that such label is suitable for immunological detection (e.g., enzyme-linked immunoassay, radioimmunoassay, fluorescent immunoassay, chemiluminescence immunoassay, etc.). Such label is well known in the art and includes, but is not limited to, enzyme (e.g., horseradish peroxidase, alkaline phosphatase, β-galactosidase, urease, glucose oxidase, etc.), radionuclide (e.g., $^3$H, $^{125}$I, $^{35}$S, $^{14}$C, or $^{32}$P), fluorescent dye (e.g., fluorescein isothiocyanate (FITC), fluorescein, tetramethylrhodamine isothiocyanate (TRITC), phycoerythrin (PE), Texas red, Rhodamine, quantum dot or cyanine derivative (e.g., Cy7, Alexa 750)), chemiluminescent substance (e.g., acridinium ester compound), and biotin for binding avidin (e.g., streptavidin) modified by the above label. The labels encompassed by the present invention can be detected by methods known in the art. For example, radioactive labels can be detected using photographic film or a scintillation calculator, and fluorescent labels can be detected using a light detector to detect the emitted light. Enzyme labels are generally detected by providing a substrate to the enzyme and detecting the reaction product produced by the action of the enzyme on the substrate. Calorimetric labels are detected by simply visualizing the coloring labels. Chemiluminescent substances (e.g., acridinium ester compound) are typically detected with the emitted light by providing the luminescent substance with a trigger solution and/or a catalyst. Biotin is typically detected by providing biotin with an avidin (e.g., streptavidin) modified by the label as described above and detecting the label carried by the avidin linked to the biotin. In certain embodiments, the detectable label as described above can be attached to the antibody or antigen-binding fragment thereof of the present invention via a linker with varying lengths to reduce potential steric hindrance.

In certain embodiments, the detectable label is selected from enzyme (e.g., horseradish peroxidase or alkaline phosphatase), chemiluminescent reagent (e.g., acridinium ester compound), fluorescent dye, or biotin.

In certain embodiments, the kit may further comprise a reagent for enabling detection of the corresponding detectable label. For example, when the detectable label is an enzyme, the kit may further comprise a chromogenic substrate for the corresponding enzyme, such as o-phenylenediamine (OPD), tetramethylbenzidine (TMB), ABTS or luminol compound for horseradish peroxidase; or p-nitrophenyl phosphate (p-NPP) or AMPPD for alkaline phosphatase. For example, when the detectable label is a chemiluminescent reagent (e.g., an acridinium ester compound), the kit may further comprise a pre-trigger solution and/or a trigger solution for chemiluminescence.

In certain embodiments, the kit further comprises a solid carrier. In certain embodiments, the solid carrier comprises a well plate, test tube, bead (e.g., latex particle) or membrane (e.g., nitrocellulose membrane) made of or coated with a polymeric material (e.g., polyvinyl chloride, polystyrene, polyacrylamide or cellulose), or a magnetic bead pre-coated with a functional group (e.g., amino, carboxyl, biotin or avidin). In certain embodiments, the solid carrier is selected from magnetic bead or microtiter plate (e.g., microwell plate or ELISA plate).

In certain embodiments, the kit further comprises a coating reagent such as a coating buffer (e.g., carbonate buffer, phosphate buffer, phosphate buffer, Tris-HCL buffer, or borate buffer) for coating the first antibody on the solid carrier. Methods for coating proteins or polypeptides on solid carriers are well known in the art, including for example physical adsorption, covalent coupling via aminated or carboxylated surfaces, or binding mediated by avidin-biotin system, polylysine pre-coated surface, protein A or protein G pre-coated surface.

In certain embodiments, the first antibody is coated on the surface of the solid carrier.

In certain embodiments, the kit comprises at least the solid carrier and the first antibody in separate containers or in separate compartments of a single container unit.

In certain exemplary embodiments, the kit comprises: a first antibody, and a second antibody bearing a detectable label. In certain exemplary embodiments, the kit comprises: a first antibody coated on the surface of a solid carrier, and a second antibody bearing a detectable label. In certain exemplary embodiments, the kit comprises: one or more kinds of first antibodies, and a secondary antibody bearing a detectable label. In certain exemplary embodiments, the kit comprises: one or more kinds of first antibodies coated on the surface of a solid carrier, and a secondary antibody bearing a detectable label. In certain embodiments, the more kinds of first antibodies recognize different epitopes contained in positions 150-183 of the HBcAg protein.

In certain embodiments, the kit further comprises a lysing agent for lysing HBV virions. Herein, the lysing agent for lysing HBV virions refers to any agent capable of lysing Dane particles (i.e., disrupting viral envelope) to expose HBcAg antigen. Such agent is known to those skilled in the art, including for example surfactant such as NP40, LDS or SDS.

In certain embodiments, the lysing agent comprises LDS or SDS. In certain embodiments, the kit further comprises a neutralizing agent, in which the neutralizing agent comprises CHAPS. In certain embodiments, the lysing agent comprises 20% LDS or 20% SDS. In certain embodiments, the lysing agent comprises 20% LDS or 20% SDS and the balance water. In certain embodiments, the neutralizing agent comprises 10% CHAPS. In certain embodiments, the neutralizing agent comprises 10% CHAPS, 20 mM PBS. In certain embodiments, the neutralizing agent comprises 10% CHAPS, 20 mM PBS, and the balance water.

In certain embodiments, the kit further comprises one or more reagents or devices selected from the group consisting of: a standard (e.g., a series of samples containing different known amounts of HBcAg); a positive control sample (e.g., a sample containing a known amount of HBcAg); a negative control sample (e.g., a sample free of HBcAg); a lysing agent (and optionally a neutralizing agent) for lysing HBV virus; and, a device for collecting or storing a sample to be tested (e.g., a blood collection device).

Preparation of Antibodies

The first antibody and the second antibody described in the first aspect can be prepared by various methods known in the art, such as by genetic engineering recombinant technology. For example, DNA molecules encoding the heavy and light chain genes of the antibodies of the present invention can be obtained by chemical synthesis or PCR amplification. The resulting DNA molecules can be inserted into an expression vector and then transfected into a host cell. Then, the transfected host cell can be cultured under specific conditions to express the antibodies of the present invention.

The antigen-binding fragment described in the first aspect can be obtained by hydrolysis of intact antibody molecules (see: Morimoto et al., J. Biochem. Biophys. Methods 24:107-117 (1992) and Brennan et al., Science 229:81 (1985)). Alternatively, these antigen-binding fragments can also be produced directly by recombinant host cells (reviewed in Hudson, Curr. Opin. Immunol. 11:548-557 (1999); Little et al., Immunol. Today, 21:364-370 (2000)). For example, Fab' fragments can be obtained directly from host cells; Fab' fragments can be chemically coupled to form F(ab')$_2$ fragments (Carter et al., Bio/Technology, 10: 163-167 (1992)). In addition, Fv, Fab or F(ab')$_2$ fragments can also be directly isolated from the culture medium of recombinant host cells. Other techniques for preparing these antigen-binding fragments are well known to those of ordinary skill in the art.

Therefore, in a second aspect, the present invention provides a kit, which comprises:

(i) a first antibody, an isolated nucleic acid molecule encoding the first antibody, a vector comprising the isolated nucleic acid molecule, or a recombinant cell expressing the first antibody; wherein the first antibody is defined as in the first aspect; and, (ii) a second antibody, an isolated nucleic acid molecule encoding the second antibody, a vector comprising the isolated nucleic acid molecule, or a recombinant cell expressing the second antibody; wherein the second antibody is defined as in the first aspect.

In certain embodiments, the vector is a cloning vector or an expression vector. In certain embodiments, the vector is, for example, a plasmid, cosmid, phage, and the like.

In certain embodiments, the recombinant cell expressing the first antibody is a host cell comprising an isolated nucleic acid molecule encoding the first antibody or a vector comprising the isolated nucleic acid molecule; the recombinant cell expressing the second antibody is a host cell comprising an isolated nucleic acid molecule encoding the second antibody or a vector comprising the isolated nucleic acid molecule. Such host cells include, but are not limited to, prokaryotic cells such as E. coli cells, and eukaryotic cells such as yeast cells, insect cells, plant cells, and animal cells (e.g., mammalian cells, such as mouse cells, human cells, etc.). In certain embodiments, the host cells of the present invention are mammalian cells, for example, CHO (e.g., CHO-K1, CHO-S, CHO DG44).

In certain embodiments, the recombinant cell expressing the first antibody is a hybridoma cell line 18B2-2, which is deposited in the China Center for Type Culture Collection (CCTCC) and has the deposit number of CCTCC NO. C2019303; and, the recombinant cell expressing the second antibody is a hybridoma cell line 2A7, which is deposited in the China Center for Type Culture Collection (CCTCC) and has the deposit number of CCTCC NO. C2019302.

Detection Method and Use

In a third aspect, the present invention provides a method for detecting the presence or level of HBcAg protein in a sample, comprising the steps of:

(1) contacting the sample with a first antibody to form an antibody-antigen complex, in which the first antibody is defined as in the first aspect;

(2) contacting the antibody-antigen complex with a second antibody to form an antibody-antigen-antibody complex, in which the second antibody is defined as in the first aspect; and (3) determining an amount of the antibody-antigen-antibody complex.

The method may be used for diagnostic purposes, or for non-diagnostic purposes. In certain embodiments, the method of the present invention is used for non-diagnostic purposes. In such embodiments, the sample to be tested is known to contain HBcAg, that is, the subject of the sample has been diagnosed prior to the detection by the method of the present invention; therefore, the method of the present invention is of no help to the diagnosis of the sample. Thus, the direct purpose of the method of the present invention is not to obtain the diagnostic result of the subject of the sample, but to perform further accurate quantitative detection on the sample with known diagnostic information.

In some embodiments, the second antibody bears a detectable label. In certain embodiments, the determining described in step (3) comprises the steps of: (3a) detecting an amount of the detectable label; (3b) comparing the amount of detectable label obtained in step (3a) with a standard curve of the relationship between the known amount of HBcAg and the amount of the detectable label, thereby obtaining the content of HBcAg. In certain embodiments, the determining described in step (3) comprises the steps of: (3a) detecting an amount (e.g., luminescence value) of the detectable label; (3b) comparing the amount (e.g., luminescence value) of detectable label obtained in step (3a) with a Cut off value, when the ratio is less than 1, the sample is considered to be negative, and when the ratio is greater than or equal to 1, the sample is considered to be HBcAg positive. In certain embodiments, when the detectable label is an acridinium ester compound, the Cut off value is 9000.

In other embodiments, the second antibody bears no detectable label. In such embodiments, the determining described in step (3) comprises: using a third antibody bearing a detectable label to detect the antibody-antigen-antibody complex. In certain embodiments, the third antibody is capable of specifically binding to the second antibody (e.g., capable of specifically binding to a constant region of the second antibody). In certain embodiments, the determining described in step (3) may comprise the steps of: (3a) contacting the antibody-antigen-antibody complex with a third antibody bearing a detectable label; (3b) detecting an amount of the detectable label; (3c) comparing the amount of detectable label obtained in step (3b) with a standard curve of the relationship between the known amount of HBcAg and the amount of the detectable label, thereby obtaining the content of HBcAg. In certain embodiments, the determining described in step (3) comprises the steps of: (3a) contacting the antibody-antigen-antibody complex with a third antibody bearing a detectable label; (3b) detecting an amount (e.g., luminescence value) of detectable label; (3c) comparing the amount (e.g., luminescence value) of detectable label obtained in step (3b) with a Cut off value, when the ratio is less than 1, the sample is considered to be negative, when the ratio is greater than or equal to 1, the sample is considered to be HBcAg positive.

In certain embodiments, when the detectable label is an acridinium ester compound, the Cut off value is 9000.

In certain embodiments, the detectable label is selected from the group consisting of enzyme (e.g., horseradish peroxidase or alkaline phosphatase), chemiluminescent reagent (e.g., acridinium ester compound), fluorescent dye, or biotin.

In certain embodiments, in step (3), the determining is selected from enzyme immunoassay or chemiluminescence immunoassay.

In certain embodiments, prior to step (1), the method further comprises a step of treating the sample, the treating comprising: mixing a lysing agent with the sample to lyse virus. In certain embodiments, the treating further comprises terminating the lysis reaction with a neutralizing agent.

In certain embodiments, the lysing agent, neutralizing agent are defined as in the first aspect.

In certain embodiments, the first antibody is coated on the surface of a solid carrier. In certain embodiments, the solid carrier is selected from the group consisting of magnetic bead or microtiter plate (e.g., microwell plate or ELISA plate).

In certain embodiments, a washing step is further comprised before step (2) and/or step (3). The washing step can remove unreacted substances.

In certain embodiments, the sample is selected from whole blood, plasma, and serum.

In another aspect, the present invention also relates to a use of the kit according to the first aspect in the manufacture of a detection kit for detecting the presence or level of HBcAg protein in a sample.

In certain embodiments, the kit is used to detect the presence or level of HBcAg protein in a sample by the method according to the third aspect.

2A7 mAb and Use Thereof

The anti-HBcAg antibodies currently used in the HBcAg immunological detection (such as immunohistochemistry or immunofluorescence) of tissue or cell samples are polyclonal antibodies. Polyclonal antibodies can improve the detection sensitivity, but often have shortcomings such as high background and lower specificity, and difficulty in standardization of immunohistochemical results. However, there is no report on the use of anti-HBcAg monoclonal antibodies for the immunological detection of HBcAg in tissue or cell samples.

The present inventors unexpectedly found a monoclonal antibody suitable for the immunological detection of HBcAg in a tissue or cell sample, and the detection effect based on the monoclonal antibody can reach a level comparable to that of commercial polyclonal antibodies, which is a remarkable, unexpected and very favorable technical effect.

Therefore, in the fourth aspect, the present invention also provides a monoclonal antibody or antigen-binding fragment thereof capable of specifically binding to HBcAg, wherein, (i) the monoclonal antibody or antigen-binding fragment thereof comprises: a heavy chain variable region (VH) comprising the following 3 complementarity determining regions (CDRs): HCDR1 having a sequence set forth in SEQ ID NO: 11, HCDR2 having a sequence set forth in SEQ ID NO: 12, and HCDR3 having a sequence set forth in SEQ ID NO: 13; and/or, a light chain variable region (VL) comprising the following 3 complementarity determining regions (CDRs): LCDR1 having a sequence set forth in SEQ ID NO: 14, LCDR2 having a sequence set forth in SEQ ID NO: 15, and LCDR3 having a sequence set forth in SEQ ID NO: 16; or, (ii) the monoclonal antibody or antigen-binding fragment thereof comprises: a heavy chain variable region (VH) comprising 3 CDRs contained in a heavy chain variable region set forth in SEQ ID NO: 9; and/or, a light chain variable region (VL) comprising 3 CDRs contained in a light chain variable region set forth in SEQ ID NO:

10; preferably, the 3 CDRs contained in the heavy chain variable region and/or the 3 CDRs contained in the light chain variable region are defined by the Kabat, Chothia or IMGT numbering system; or, (iii) the monoclonal antibody is a monoclonal antibody produced by a hybridoma cell line 2A7 which is deposited in the China Center for Type Culture Collection (CCTCC) and has the deposit number of CCTCC NO. C2019302.

In certain embodiments, the monoclonal antibody or antigen-binding fragment thereof comprises:

(a) a heavy chain variable region (VH) comprising an amino acid sequence selected from the group consisting of: (i) a sequence set forth in SEQ ID NO: 9; (ii) a sequence having a substitution, deletion or addition of one or several amino acids (e.g., substitution, deletion or addition of 1, 2, 3, 4 or 5 amino acids) as compared with the sequence set forth in SEQ ID NO: 9; or (iii) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence set forth in SEQ ID NO: 9;

and/or, (b) a light chain variable region (VL) comprising an amino acid sequence selected from the group consisting of: (iv) a sequence set forth in SEQ ID NO: 10; (v) a sequence having a substitution, deletion or addition of one or several amino acids (e.g., substitution, deletion or addition of 1, 2, 3, 4 or 5 amino acids) as compared with the sequence set forth in SEQ ID NO: 10; or (vi) a sequence having a sequence identity of at least 80%, at least 85%, at least 90%, at least 91%, at least 92%, at least 93%, at least 94%, at least 95%, at least 96%, at least 97%, at least 98%, at least 99%, or 100% as compared with the sequence set forth in SEQ ID NO: 10.

In certain embodiments, the substitutions described in (ii) or (v) are conservative substitutions.

In certain embodiments, the monoclonal antibody or antigen-binding fragment thereof comprises: a VH having the sequence set forth in SEQ ID NO:9 and a VL having the sequence set forth in SEQ ID NO:10.

In certain embodiments, the monoclonal antibody comprises a heavy chain constant region (CH) and a light chain constant region (CL). In certain embodiments, the monoclonal antibody is an IgG, IgM, IgE, IgD or IgA antibody.

In certain embodiments, the antigen-binding fragment is selected from the group consisting of Fab, Fab', (Fab')$_2$, Fv, disulfide-linked Fv, scFv, diabody, and single domain antibody (sdAb).

In certain embodiments, the monoclonal antibody is a murine antibody, chimeric antibody, or humanized antibody.

In another aspect, the present invention also relates to a use of the monoclonal antibody or antigen-binding fragment thereof according to the fourth aspect in the manufacture of a reagent for detecting HBcAg in a sample.

In certain embodiments, the sample is a tissue sample (e.g., a tissue section) or a cell sample.

In certain embodiments, the detection is an immunological detection. In certain embodiments, the immunological detection is selected from the group consisting of Immunohistochemistry (IHC), Immunocytochemistry (ICC), Immunofluorescence (IF) and Western Blot.

In one embodiment, the monoclonal antibody or antigen-binding fragment thereof bears a detectable label.

In another embodiment, the reagent for detecting HBcAg in a sample further comprises a secondary antibody bears a detectable label.

In certain embodiments, the secondary antibody is specific for an antibody of the species (e.g., mouse) from which the constant region contained in the monoclonal antibody or antigen-binding fragment thereof is derived.

In certain embodiments, the secondary antibody is an anti-immunoglobulin antibody, for example, an anti-IgG antibody.

In certain embodiments, the detectable label is selected from enzyme (e.g., horseradish peroxidase or alkaline phosphatase), fluorescent dye, or biotin.

In certain exemplary embodiments, when the immunological detection is selected from immunohistochemistry (IHC), immunocytochemistry (ICC), or Western Blot, the detectable marker is selected from enzyme.

In certain exemplary embodiments, when the immunological detection is selected from immunofluorescence (IF), the detectable label is selected from fluorescent dye.

Definition of Terms

In the present invention, unless otherwise specified, scientific and technical terms used herein have the meanings commonly understood by those skilled in the art. Moreover, the laboratory procedures of virology, biochemistry, and immunology used in herein are all routine procedures widely used in the corresponding fields. Meanwhile, for a better understanding of the present invention, definitions and explanations of related terms are provided below.

As used herein, the term "HBcAg" refers to core antigen of hepatitis B virus (HBV), also known as the nucleocapsid protein, which is well known to those skilled in the art (see, for example, NCBI GENBANK database accession number: GU357842.1). HBcAg protein contains an assembly region at its N-terminus that is involved in VLP assembly, and an arginine-rich domain (Arginine Rich Domain, ARD) at its C-terminus.

As used herein, when referring to the amino acid sequence of HBcAg, it is described using the sequence set forth in SEQ ID NO:17. For example, the expression "amino acid residues 150-183 of HBcAg" refers to amino acid residues at positions 150-183 of the polypeptide set forth in SEQ ID NO:17. However, those skilled in the art understand that a mutation or variation (including, but not limited to, substitution, deletion and/or addition, such as HBcAg of different genotypes or subgenotypes) can be naturally generated or artificially introduced in the amino acid sequence of HBcAg, without affecting its biological function. Thus, in the present invention, the term "HBcAg" shall include all such sequences, including, for example, the sequence set forth in SEQ ID NO: 17 and natural or artificial variants thereof. In addition, when describing a sequence fragment of HBcAg, it includes not only a sequence fragment of SEQ ID NO: 17, but also a corresponding sequence fragment in its natural or artificial variant. For example, the expression "amino acid residues 150-183 of HBcAg" includes, amino acid residues 150-183 of SEQ ID NO: 17, and corresponding fragments in variant (natural or artificial) thereof. According to the present invention, the expression "corresponding sequence fragment" or "corresponding fragment" refers to a fragment located in an equivalent position of the sequences being compared for optimal alignment, i.e., alignment of the sequences to obtain the highest percent identity.

As used herein, the term "Dane particle", also known as large spherical particle, refers to an intact infectious hepatitis B virus particle with a double-layered structure. HBcAg is usually present in the core of Dane particle. Therefore, in order to detect HBcAg, it is typically necessary to lyse the outer shell of Dane particle first, so that the HBcAg can be exposed and free.

As used herein, the term "specific binding" refers to a non-random binding reaction between two molecules (i.e., a binding molecule and a target molecule), such as a reaction between an antibody and an antigen to which it is directed. The binding affinity between two molecules can be described by $K_D$ value. The $K_D$ value is a dissociation constant derived from the ratio of kd (dissociation rate of a specific binding molecule-target molecule interaction; also known as koff) to ka (association rate of a specific binding molecule-target molecule interaction; also known as kon), or kd/ka expressed as molar concentration (M). The smaller the $K_D$ value, the tighter the binding between the two molecules and the higher the affinity. In certain embodiments, an antibody that specifically binds to an antigen (or an antibody specific for an antigen) refers to an antibody that binds the antigen with an affinity ($K_D$) of less than about $10^{-5}$ M, such as less than about $10^{-6}$ M, $10^{-7}$ M, $10^{-8}$ M, $10^{-9}$ M or $10^{-10}$ M or less. $K_D$ values can be determined by methods well known in the art, such as in a BIACORE instrument using surface plasmon resonance (SPR).

As used herein, the term "immunological assay" refers to an assay that utilizes the specific interaction/binding affinity between antigen and antibody, which can generally be used to detect the presence or level of a specific antigen or antibody in a sample. Such immunological assays are well known to those skilled in the art and include, but are not limited to, enzyme immunoassay (EIA), chemiluminescence immunoassay (CLIA), radioimmunoassay (RIA), fluorescence immunoassay (FIA), Western blotting, immunoturbidimetric method, surface plasmon resonance method, etc. For a detailed description of immunological assays, see, for example, Fundamental Immunology, Ch. 7 Paul, W., ed., 2nd ed., Raven Press, N.Y. (1989).

As used herein, the term "antibody" refers to an immunoglobulin molecule generally composed of two pairs of polypeptide chains, each pair having one light chain (LC) and one heavy chain (HC). Antibody light chains can be classified as κ (kappa) and λ (lambda) light chains. Heavy chains can be classified as μ, δ, γ, α, or ε, and accordingly the isotypes of antibody are defined as IgM, IgD, IgG, IgA and IgE, respectively. Within the light and heavy chains, variable and constant regions are linked by a "J" region of about 12 or more amino acids, and the heavy chain also contains a "D" region of about 3 or more amino acids. Each heavy chain consists of a heavy chain variable region (VH) and a heavy chain constant region (CH). The heavy chain constant region consists of 3 domains (CH1, CH2 and CH3). Each light chain consists of a light chain variable region (VL) and a light chain constant region (CL). The light chain constant region consists of one domain, CL. Constant domains are not directly involved in the binding of antibody to antigen, but exhibit a variety of effector functions, such as mediating the binding of immunoglobulin with host tissue or factor, including various cells of the immune system (e.g., effector cells) and classical complement system first component (C1q). VH and VL regions can also be subdivided into regions of high variability (called complementarity determining regions (CDRs) interspersed with more conserved regions called framework regions (FRs). Each VH and VL consists of 3 CDRs and 4 FRs arranged in the following order: FR1, CDR1, FR2, CDR2, FR3, CDR3, FR4 from the amino terminus to the carboxy terminus. The variable regions (VH and VL) of each heavy chain/light chain pair form the antigen binding site. The assignment of amino acids to regions or domains can follow the definitions of Kabat, Sequences of Proteins of Immunological Interest (National Institutes of Health, Bethesda, Md. (1987 and 1991)), or Chothia & Lesk (1987) J. Mol. Biol. 196:901-917; definition by Chothia et al. (1989) Nature 342:878-883.

As used herein, the term "complementarity determining region" or "CDR" refers to the amino acid residues in the variable region of an antibody that are responsible for antigen binding. The variable regions of the heavy and light chains each contain three CDRs, designated CDR1, CDR2 and CDR3. The precise boundaries of these CDRs can be defined according to various numbering systems known in the art, for example according to the Kabat numbering system (Kabat et al., Sequences of Proteins of Immunological Interest, 5th Ed. Public Health Service, National Institutes of Health, Bethesda, Md., 1991), the Chothia numbering system (Chothia & Lesk (1987) J. Mol. Biol. 196:901-917; Chothia et al. (1989) Nature 342:878-883), or the IMGT numbering system (Lefranc et al. al., Dev. Comparat. Immunol. 27:55-77, 2003). For a given antibody, those skilled in the art will readily identify the CDRs defined by each numbering system. Also, correspondence between different numbering systems is well known to those skilled in the art (see, for example, Lefranc et al., Dev. Comparat. Immunol. 27:55-77, 2003).

In the present invention, the CDRs contained in the antibody or antigen-binding fragment thereof of the present invention can be determined according to various numbering systems known in the art. In certain embodiments, the CDRs contained in the antibody or antigen-binding fragment thereof of the present invention are preferably determined by the Kabat, Chothia or IMGT numbering system. In certain embodiments, the CDRs contained in the antibody or antigen-binding fragment thereof of the present invention are preferably identified by the Kabat numbering system.

As used herein, the term "framework region" or "FR" residues refers to those amino acid residues in the variable region of an antibody other than the CDR residues as defined above.

The term "antibody" is not limited by any particular method of producing the antibody. For example, it includes recombinant antibody, monoclonal antibody and polyclonal antibody. Antibody can be of different isotypes, for example, IgG (e.g., IgG1, IgG2, IgG3, or IgG4 subtype), IgAQ1, IgA2, IgD, IgE, or IgM antibody.

As used herein, the term "antigen-binding fragment" of an antibody refers to a polypeptide comprising a fragment of a full-length antibody that retains the ability to specifically bind to the same antigen to which the full-length antibody binds, and/or competes with the full-length antibody to specifically bind the antigen, which is also referred to as an "antigen binding portion". See generally, Fundamental Immunology, Ch. 7 (Paul, W., ed., 2nd ed., Raven Press, NY (1989), which is hereby incorporated by reference in its entirety for all purposes. Antigen-binding fragments of antibodies can be produced by recombinant DNA techniques or by enzymatic or chemical cleavage of intact antibodies. Non-limiting examples of antigen-binding fragments include Fab, Fab', F(ab')$_2$, Fd, Fv, complementarity determining region (CDR) fragment, scFv, diabody, single domain antibody, chimeric antibody, linear antibody, nanobody (the technology comes from Domantis), and polypeptide that comprises at least a portion of an antibody sufficient to confer specific antigen-binding capacity to the polypeptide. Engineered antibody variants are reviewed in Holliger et al., 2005; Nat Biotechnol, 23: 1126-1136.

As used herein, the term "full-length antibody" refers to an antibody consisting of two "full-length heavy chains" and two "full-length light chains". Wherein, "full-length heavy chain" refers to a polypeptide chain consisting of a heavy chain variable region (VH), a heavy chain constant region CH1 domain, a hinge region (HR), a heavy chain constant region CH2 domain, a heavy chain constant region CH3 domain; and, when the full-length antibody is of the IgE isotype, it optionally comprises a heavy chain constant region CH4 domain. Preferably, a "full-length heavy chain" is a polypeptide chain consisting of VH, CH1, HR, CH2 and CH3 in the N-terminal to C-terminal direction. A "full-length light chain" is a polypeptide chain consisting of a light chain variable region (VL) and a light chain constant region (CL) in the N-terminal to C-terminal direction. The two pairs of full-length antibody chains are linked together by a disulfide bond between CL and CH1 and a disulfide bond between the HRs of the two full-length heavy chains. The full-length antibody of the present invention can be derived from a single species, such as human; it can also be a chimeric antibody or a humanized antibody. The full-length antibody of the present invention comprises two antigen-binding sites formed by VH and VL pairs which specifically recognize/bind to the same antigen.

As used herein, the term "Fd" refers to an antibody fragment consisting of VH and CH1 domains; the term "dAb fragment" refers to an antibody fragment consisting of a VH domain (Ward et al., Nature 341:544546 (1989)); the term "Fab fragment" refers to an antibody fragment consisting of VL, VH, CL and CH1 domains; the term "F(ab')$_2$ fragment" refers to an antibody fragment comprising two Fab fragments linked via a disulfide bond of the hinge region; the term "Fab' fragment" refers to a fragment obtained by reducing the disulfide bond linking two heavy chain fragments in an F(ab')$_2$ fragment, which consists of an intact light chain and a heavy chain Fd fragment (consisting of VH and CH1 domains).

As used herein, the term "Fv" means an antibody fragment consisting of VL and VH domains of one arm of an antibody. Fv fragment is generally considered to be the smallest antibody fragment that can form a complete antigen-binding site. It is generally believed that the six CDRs confer antigen-binding specificity to an antibody. However, only one variable region (e.g., an Fd fragment, which contains only three antigen-specific CDRs) is able to recognize and bind an antigen, albeit with possibly lower affinity than the intact binding site.

As used herein, the term "Fc" refers to an antibody fragment formed by linking the second and third constant regions of the first heavy chain of an antibody with the second and third constant regions of the second heavy chain by disulfide bonds. The Fc fragment of an antibody has many different functions, but is not involved in antigen binding.

As used herein, the term "scFv" refers to a single polypeptide chain comprising VL and VH domains, wherein the VL and VH are connected by a linker (see, for example, Bird et al., Science 242:423-426 (1988); Huston et al., Proc. Natl. Acad. Sci. USA 85:5879-5883 (1988); and Pluckthun, The Pharmacology of Monoclonal Antibodies, Vol. 113, Eds. Roseburg and Moore, Springer-Verlag, New York, pp. 269-315 (1994)). Such scFv molecules can have the general structure: NH$_2$—VL-linker-VH—COOH or NH$_2$—VH-linker-VL-COOH. Suitable prior art linker consists of repeated GGGGS (SEQ ID NO:50) amino acid sequences or variants thereof. For example, a linker with the amino acid sequence (GGGGS (SEQ ID NO:50))$_4$ or variants thereof can be used (Holliger et al. (1993), Proc. Natl. Acad. Sci. USA 90: 6444-6448). Other linkers useful in the present invention are described by Alfthan et al. (1995), Protein Eng. 8:725-731, Choi et al. (2001), Eur. J. Immunol. 31:94-106, Hu et al. (1996), Cancer Res. 56:3055-3061, described by Kipriyanov et al. (1999), J. Mol. Biol. 293:41-56 and Roovers et al. (2001), Cancer Immunol. In some cases, a disulfide bond may also exist between the VH and VL of scFv.

As used herein, the term "diabody" means that its VH and VL domains are expressed on a single polypeptide chain, but the linker used is too short to allow pairing between the two domains of the same chain, thereby forcing the domains to pair with the complementary domains of another chain and generate two antigen binding sites (see, for example, Holliger P. et al., Proc. Natl. Acad. Sci. USA 90:6444-6448 (1993), and Poljak R J et al, Structure 2:1121-1123 (1994)).

As used herein, the term "single-domain antibody (sdAb)" has the meaning commonly understood by those of skill in the art, which refers to an antibody fragment composed of a single monomeric variable antibody domain (e.g., a single heavy chain variable region) that retains the ability to specifically bind to the same antigen to which the full-length antibody binds. Single domain antibody is also known as nanobody.

Each of the aforementioned antibody fragments retains the ability to specifically bind to the same antigen to which the full-length antibody binds, and/or compete with the full-length antibody for specific binding to the antigen.

Antigen-binding fragments of antibody (e.g., the antibody fragments described above) can be obtained from a given antibody (e.g., the antibody provided herein) using conventional techniques known to those of skill in the art (e.g., recombinant DNA techniques or enzymatic or chemical fragmentation methods), and the antigen-binding fragments of antibody can be screened for specificity by the same manner as used for the intact antibody.

Herein, unless specified definitely, when the term "antibody" is referred to, it includes not only the intact antibody but also antigen-binding fragments of the antibody.

As used herein, the term "chimeric antibody" refers to an antibody in which a portion of its light or/and heavy chain is derived from an antibody (which may be derived from a particular species or belong to a particular antibody class or subclass), while another portion of its light chain or/and heavy chain is derived from another antibody (which may be derived from the same or different species or belong to the same or different antibody class or subclass), but nevertheless, it still retains the binding activity to the target antigen (U.S. Pat. No. 4,816,567 to Cabilly et al.; Morrison et al., Proc. Natl. Acad. Sci. USA, 81:6851 6855 (1984)). For example, the term "chimeric antibody" may include such an antibody (e.g., human-murine chimeric antibody) in which the heavy and light chain variable regions of antibody are derived from a first antibody (e.g., a murine antibody) and the heavy and light chain variable regions of antibody are derived from a second antibody (e.g., a human antibody).

As used herein, the term "humanized antibody" refers to a genetically engineered non-human antibody, the amino acid sequence of which has been modified to increase homology to the sequence of human antibody. Generally, all or part of the CDR regions of a humanized antibody are derived from a non-human antibody (donor antibody), and all or part of the non-CDR regions (e.g., variable FR and/or constant regions) are derived from human immunoglobulin (receptor antibody). Humanized antibody generally retains the expected properties of the donor antibody, including, but not limited to, antigen specificity, affinity, reactivity, and the like. The donor antibody can be a murine, rat, rabbit, or non-human primate (e.g., cynomolgus monkey) antibody with the desired properties (e.g., antigen specificity, affinity, reactivity, etc.).

The chimeric antibody or humanized antibody of the present invention can be prepared based on the sequence of the murine monoclonal antibody prepared above. The DNA encoding the heavy and light chains can be obtained from a target murine hybridoma and engineered to contain a non-murine (e.g., human) immunoglobulin sequence using a standard molecular biology technique.

To prepare a chimeric antibody, a murine immunoglobulin variable region can be linked to a human immunoglobulin constant region using a method known in the art. For example, the DNA encoding VH can be operably linked to another DNA molecule encoding the heavy chain constant region to obtain a full-length heavy chain gene. The sequences of human heavy chain constant region gene are known in the art (see, for example, Kabat, E A et al. (1991), Sequences of Proteins of Immunological Interest, Fifth Edition, U.S. Department of Health and Human Services, NIH Publication No. 91-3242), and the DNA fragment containing these regions can be obtained by standard PCR amplification. The heavy chain constant region may be an IgG1, IgG2, IgG3, IgG4, IgA, IgE, IgM or IgD constant region, but is generally preferably an IgG1 or IgG4 constant region. For example, the DNA encoding VL is operably linked to another DNA molecule encoding the light chain constant region CL to obtain a full-length light chain gene (as well as a Fab light chain gene). The sequences of human light chain constant region gene are known in the art (see, for example, Kabat, E A et al. (1991), Sequences of Proteins of Immunological Interest, Fifth Edition, U.S. Department of Health and Human Services, NIH Publication No. 91-3242), and the DNA fragment containing these regions can be obtained by standard PCR amplification. The light chain constant region may be a κ or λ constant region, but is generally preferably a κ constant region.

To prepare a humanized antibody, a murine CDR region can be grafted into human framework sequences using a method known in the art (see U.S. Pat. No. 5,225,539 to Winter; U.S. Pat. Nos. 5,530,101; 5,585,089; 5,693,762 and 6,180,370 to Queen et al; and Lo, Benny, KC, editor, in Antibody Engineering: Methods and Protocols, volume 248, Humana Press, New Jersey, 2004).

As used herein, the term "vector" refers to a nucleic acid delivery vehicle into which a polynucleotide can be inserted. When the vector can express the protein encoded by the inserted polynucleotide, the vector is called an expression vector. The vector can be introduced into a host cell by transformation, transduction or transfection, so that the genetic material elements carried by it can be expressed in the host cell. Vectors are well known to those skilled in the art and include, but are not limited to: plasmid; phagemid; cosmid; artificial chromosome, such as yeast artificial chromosome (YAC), bacterial artificial chromosome (BAC) or P1 derived artificial chromosome (PAC); phage such as λ phage or M13 phage and animal virus. Animal viruses that can be used as vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40). A vector may contain a variety of elements that control expression, including, but not limited to, promoter sequence, transcription initiation sequence, enhancer sequence, selection element, and reporter gene. Additionally, the vector may also contain an origin of replication site.

As used herein, the term "host cell" refers to a cell into which a vector can be introduced, including, but not limited to, prokaryotic cell such as *E. coli* or *Bacillus subtilis*, fungal cell such as yeast cell or *Aspergillus*, etc., insect cell such as S2 *Drosophila* cell or Sf9, or animal cell such as fibroblast, CHO cell, COS cell, NSO cell, HeLa cell, BHK cell, HEK 293 cell or human cell.

As used herein, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the expected properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having basic side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having 0-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl Acad. Set USA 94: 412-417 (1997), which are incorporated herein by reference).

The twenty conventional amino acids involved herein are written to follow conventional usage. See, for example, Immunology—A Synthesis (2nd Edition, E. S. Golub and D. R. Gren, Eds., Sinauer Associates, Sunderland, Mass. (1991)), which is incorporated herein by reference. In the present invention, the terms "polypeptide" and "protein" have the same meaning and are used interchangeably. And in the present invention, amino acids are generally represented by one-letter and three-letter abbreviations well known in the art. For example, alanine can be represented by A or Ala.

As used herein, the term "subject" includes, but is not limited to, various animals, particularly mammals such as human.

Beneficial Effects

The present invention provides a kit for HBcAg detection based on specific antibodies, and a double-antibody sandwich method established based on the kit. Compared with the prior art, the technical solution of the present invention can achieve a detection sensitivity comparable to that of DNA method, and can realize rapid and high-throughput detection, which has great clinical application value.

In addition, the present invention also provides an anti-HBcAg monoclonal antibody, which can be used in the field of immunological detection such as immunohistochemistry and immunofluorescence for various tissue or cell samples, having the detection effects similar to those of commercial polyclonal antibodies, and thus has broad application prospects.

The embodiments of the present invention are described in detail below with reference to the drawings and examples, but those skilled in the art will understand that the following drawings and examples are only used to illustrate the present invention, rather than limit the scope of the present invention. Various objects and advantageous aspects of the present invention will become apparent to those skilled in the art from the accompanying drawings and the following detailed description of the preferred embodiments.

SEQUENCE INFORMATION

Figure 1:
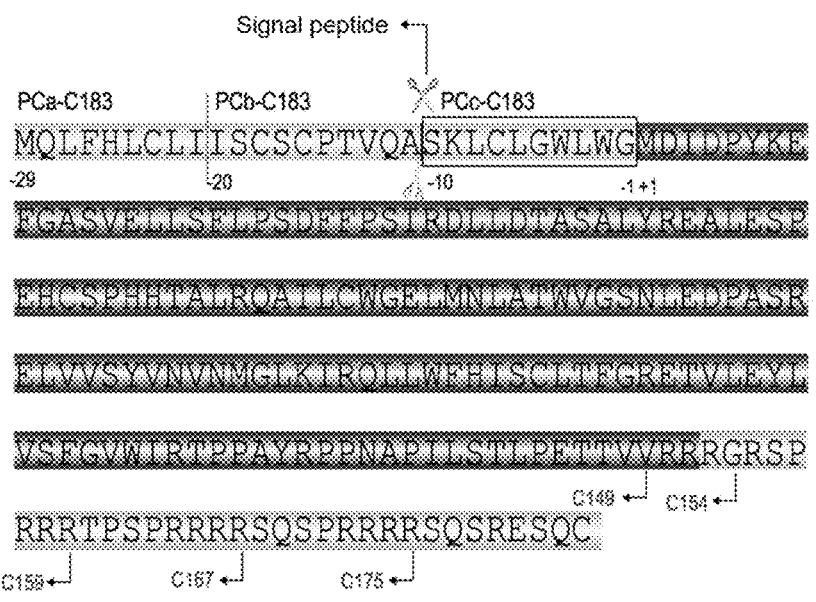
FIG. 1 shows a schematic diagram of eukaryotic expression plasmid containing HBV antigens of different lengths. SEQ ID NO: 49

Information of some sequences referred to in the present application is described in the table below.

| SEQ ID NO: | Description | Sequence information |
|---|---|---|
| 1 | 18B2-2 VH | QIQLVQSGPELKKPGETVKISCKASGYAFTDYPVHWVKQAPGKGL KWMGWINTETGEPTYADDFKGRFAFSLEASANTAYLQINNLKNED TATYFCDHYSMDYWGQGTSVTVSS |
| 2 | 18B2-2 VL | DIVITQDELSNPVTSGESVSISCRSSKSLLYKDGKTYLNWFLQRPGQ SPQLLIYLMSTRASGVSDRFSGSGSGTDFTLEISRVKAEDVGVYYC QQLVEYPFTFGSGTKLEIK |
| 3 | 18B2-2 HCDR1 | GYAFTDYP |
| 4 | 18B2-2 HCDR2 | INTETGEP |
| 5 | 18B2-2 HCDR3 | DHYSMDY |
| 6 | 18B2-2 LCDR1 | KSLLYKDGKTY |
| 7 | 18B2-2 LCDR2 | LMS |
| 8 | 18B2-2 LCDR3 | QQLVEYPFT |
| 9 | 2A7 VH | QVQLQQPGAELVKPGASVKLSCKASGYTFTRYWMHWVMQRPGQ DLEWIGEINPINGRTNYNEKFRRKATLTVDKSSSTVYIQFSSLTSED SAVYFCTREGYRNDYYYAMDFWGRGTSVTVSS |
| 10 | 2A7 VL | DIQMTQTSSSLSASPGDRVTISCRASQGINNYLNWYKQKTDGTFKL LIYYTSYLHSGVPSRFSGRGSGTDYSLTISNLEPEDVATYYCQQYG KLPWTFGGGTKLEIK |
| 11 | 2A7 HCDR1 | GYTFTRYW |
| 12 | 2A7 HCDR2 | INPINGRT |
| 13 | 2A7 HCDR3 | TREGYRNDYYYAMDF |
| 14 | 2A7 LCDR1 | QGINNY |
| 15 | 2A7 LCDR2 | YTS |
| 16 | 2A7 LCDR3 | QQYGKLPWT |
| 17 | C183 | MDIDPYKEFGASVELLSFLPSDFFPSIRDLLDTASALYREALESPEH CSPHHTALRQAILCWGELMNLATWVGSNLEDPASRELVVSYVNV NMGLKIRQLLWFHISCLTFGRETVLEYLVSFGVWIRTPPAYRPPNA PILSTLPETTVVRRRGRSPRRRTPSPRRRRSQSPRRRRSQSRESQC |

Deposit of Biological Materials:

The invention relates to the following biological materials that have been deposited in the China Center for Type Culture Collection (CCTCC, Wuhan University, Wuhan, China):

1) Hybridoma cell line 18B2-2, which has the deposit number of CCTCC NO. C2019303, and the deposit time of Nov. 28, 2019;

2) Hybridoma cell line 2A7, which has the deposit number of CCTCC NO. C2019302, and the deposit time of Nov. 28, 2019.

The address of the China Center for Type Culture Collection is Wuhan University, Wuhan 430072, P.R. China.

EXAMPLES

The present invention will now be described with reference to the following examples, which are intended to illustrate, but not limit the present invention.

Unless otherwise specified, the molecular biology experimental methods and immunoassays used in the present invention basically refer to J. Sambrook et al., Molecular Cloning: A Laboratory Manual, 2nd Edition, Cold Spring Harbor Laboratory Press, 1989, and F M Ausubel et al., Refined Laboratory Manual for Molecular Biology, 3rd Edition, John Wiley & Sons, Inc., 1995; restriction enzymes were used according to the conditions recommended by the product manufacturer. The reagents which source is not indicated in the examples are all conventional reagents in the art or commercially available reagents. Those skilled in the art appreciate that the examples describe the present invention by way of example and are not intended to limit the scope of the present invention as sought to be protected.

Example 1: Preparation of c183 Antigen 1.1 C183 clone (its sequence was set forth in SEQ ID NO: 17) was constructed, and the C183B antigen was prepared by using the *E. coli* expression system.

1.2 Purification of C183 antigen

The bacterial liquid was collected and sonicated, the sonication liquid was centrifuged at 12,000 rpm and 10° C. for 10 min, and the supernatant was collected. Then, it was allowed to stand in water bath at 65° C. for 20 min, and the supernatant was collected.

Samples were dialyzed against 1×PB7.4, followed by medium-pressure DEAE-FF chromatography (GE medium). The breakthrough peak solution (target protein) was collected, followed by purification by Capto Core700. Then the first sample peak was collected.

Example 2: Preparation of Anti-HBcAg Mouse Monoclonal Antibody 2.1 Mouse immunization 2.1.1 Preparation of immunogen: The immunogen was the HBcAg (C183 antigen) protein recombinantly expressed in *E. coli*. The recombinant antigen was diluted to 0.4 mg/mL, and mixed with an equal volume of Freund's adjuvant to form a water-in-oil emulsion (method to judge whether the mixture was completely emulsified: a small drop of the mixture was dropped on the surface of water, and if the mixture kept accumulated and did not disperse, it was considered that it had been substantially homogenized). Freund's complete adjuvant was used for the initial immunization, while incomplete Freund's adjuvant was used for the subsequent booster immunization, and no adjuvant was added for the last booster immunization 72 h before the fusion.

2.1.2 Basic immunization of mice: 6-8 week old BALB/c female mice were immunized by subcutaneous multi-point injection with the above immunogen, with the injection dose of 500 μL/mice/time, and 200 μL of eye vein blood was collected before each immunization for later titer determination. Booster immunizations were given every 2 weeks. Serum titers were measured by indirect ELISA. When the serum titers of mice reached a plateau, the immunization stopped and the mice rested for two months before the fusion.

2.1.3 Booster immunization 72 hours before fusion (Final boost): 72 hours before the fusion of mouse spleen cells and mouse myeloma cells, booster immunization of spleen was performed. The immunogen for this booster did not contain adjuvant, and 100 μl of 0.5 mg/mL recombinant protein was injected. Before the spleen immunization, the mice were anesthetized with ether, and then the abdominal skin was opened to expose the spleen, 100 μL of antigen was injected along the longitudinal direction of spleen, and then the abdominal incision was quickly sutured.

2.2 Preparation and screening of fusion hybridoma

After the booster immunization 72 h before the fusion, the mouse spleen was taken to make a cell suspension and subjected to fusion with mouse myeloma cells Sp2/0 to obtain hybridoma cells. Feeder cells were prepared prior to this. During the culture of hybridoma cells, a large number of myeloma cells and spleen cells after fusion died one after another in the 1640-HAT medium, and single cells or a few scattered cells were not easy to survive, thus other cells have to be added to make them survive. The live cells that were added were called feeder cells. In this laboratory, mouse peritoneal macrophages or 13-day-old mouse thymocytes were used as feeder cells.

2.2.1 Preparation of mouse macrophages: It was performed according to the following steps: (i) one 6-week-old BALB/c mouse was killed by stretching neck, rinsed with tap water, and soaked in 75% ethanol solution for 5 min; the mouse was placed on an ultra-clean workbench with the abdomen facing upwards; the abdominal skin of the mouse was lifted with tweezers, a small cut was made, and the skin was teared upward and downward with large tweezers to fully expose the abdomen; (ii) the peritoneum was lifted with sterile ophthalmic forceps, then an appropriate amount of culture medium was injected into the abdominal cavity with a 5 mL syringe, the limbs of the mouse were slightly lifted with another sterile eye forceps, and the culture medium was finally aspirated using a syringe and placed into a centrifuge tube; (iii) the peritoneal cell fluid was dissolved in HAT medium or HT medium to form macrophage feeder cells at a concentration of $2 \times 10^5$/mL; (iv) it was added to a 96-well cell culture plate with 0.1 mL per well, and cultured in an incubator; or it could also be directly mixed with fused cells and added to a 96-well cell culture plate.

2.2.2 Preparation of mouse thymocytes: It was performed according to the following steps: (i) one 13-day-old BALB/c mouse was sacrificed by stretching neck, rinsed with tap water, and soaked in 75% ethanol solution for 5 min; the mouse was placed on an ultra-clean workbench with the abdomen facing upwards; (ii) the mouse abdominal skin was lifted with forceps, and the outer skin of the abdomen and thorax was cut; (iii) the thoracic cavity was opened with another pair of clean scissors, the milky white thymus was taken out with tweezers, and subjected to homogenization and filtration through a 200-mesh cell sieve to obtain thymic feeder cell fluid.

2.2.3 Preparation of mouse myeloma cells: It was performed according to the following steps: (i) the mouse myeloma cell line Sp2/0-Ag14 (Sp2/0) was easy to culture and had a high fusion rate, thus was the most ideal fusion cell at present, but the Sp2/0 hybridoma cell line was more sensitive to culture conditions than NS-1 and had poor growth at the condition of excessive dilution (density below $3 \times 10^5$/mL) and alkaline pH (pH above 7.3); (ii) the cells in logarithmic growth phase were selected for the fusion; (iii) before the fusion, the myeloma cells were transferred from the culture flask into a centrifuge tube, and washed three times with RPMI-1640 medium (1000 rpm×5 min); the cells were resuspended in RPMI-1640 medium and counted; (iv) generally, the mouse myeloma cells should be resuscitated 5 days before the fusion, and about 6 flasks of 35 cm² Sp2/0 cells were needed for each fusion.

2.2.4 Preparation of immune splenocytes: It was performed according to the following steps: (i) the BALB/C mice for the fusion were sacrificed by bloodletting after removing the eyeballs, and the collected blood sample was made into antiserum, which could be used as a positive control for antibody detection. The mice were rinsed with tap water, soaked in 75% ethanol solution for 5 min, then placed on the mouse dissection board in the ultra-clean bench, in the right lateral position. (ii) the abdominal cavity was aseptically opened, the spleen was taken out, cut into small pieces with scissors and placed on a 200-mesh cell screen, then squeezed and ground with a grinding rod (inner core of syringe), and at the same time, added with RPMI-1640 medium dropwise with a pipette. (iii) an appropriate amount of RPMI-1640 culture medium was replenished, allowed to stand for 3-5 min, and 2/3 of the upper suspension was transferred into a 50 mL plastic centrifuge tube; the above process was repeated 2-3 times. (iv) the cells were washed 3 times with RPMI-1640 medium (1000 rpm×10 min). (v) the cells were resuspended in RPMI-1640 medium and counted.

2.2.5 Preparation of hybridoma by PEG-medicated fusion: It was performed according to the following steps: (1) before fusion, 1 mL of PEG-1500, 10 mL of RPMI-1640 serum-free medium and 200 mL of complete medium were pre-heated to 37° C.; (ii) the prepared myeloma cells and spleen cells were mixed in a 50 mL centrifuge tube ($1×10^8$ spleen cells+$1×10^7$ myeloma cells, about 10:1), centrifuged at 1500 rpm for 8 min; after centrifugation, the bottom of tube was gently flicked to loosen the cells to form a paste; (iii) 0.8 mL ($1×10^8$ spleen cells+0.8 mL PEG) was added into the centrifuge tube with a 1 mL pipette, stirred gently while adding, and PEG was added within 60 seconds on average, then 10 mL of the complete medium of RPMI-1640 pre-heated at 37° C. was added under gentle stirring; finally, RPMI-1640 medium was replenished to 40 mL, and centrifuged at 1000 rpm for 5 min; (iv) the supernatant was discarded, a small amount of HT medium was added to disperse the cells carefully, the cells were transferred into the prepared HT medium, added to a 96-well cell culture plate with 0.1 mL per well, and cultured in a $CO_2$ incubator; (v) after 12 hours, an appropriate amount of HAT complete medium was prepared, and added dropwise to each well with 0.1 mL per well; after 5 days, the HT complete medium was used to replace 50% to 100% the cell supernatant in the well; after about 9 to 14 days, the supernatant was collected for detection.

2.2.6 Screening of hybridoma: Indirect ELISA was used for screening, coating with 100 ng/mL recombinant antigen was performed with 0.1 mL per well, then 50 μL of cell supernatant was added for detection, and positive clone wells were selected.

2.2.7 Cloning of hybridoma cells: By using the limiting dilution method, the cells were firstly diluted in series to according to a certain concentration, and then inoculated into each well of a 96-well cell culture plate, so that only one cell grew in the well as much as possible; the positive clone of hybridoma generally needed to be cloned 2-3 times until it was 100% positive and confirmed as a stable clone.

2.3 Production of monoclonal antibody ascites 2-3 BALB/c mice were injected with 0.5 mL of liquid paraffin oil into the abdominal cavity. After 1 week, the hybridoma cells in logarithmic growth phase were centrifuged at 1000 rpm for 5 min, and the supernatant was discarded. The hybridoma cells were suspended with serum-free medium, and the number of cells was adjusted to ($1-2$)×$10^6$/mL, and 0.5 mL of the cells was injected intraperitoneally into each mouse. After 7-10 days, the abdomen of the mice was obviously enlarged, and the mice were sacrificed by stretching neck, rinsed with tap water, soaked in 75% ethanol for 5 min, and the limbs of mouse were fixed with injection needles on the mouse dissection table with the abdomen facing up. The abdominal skin of mouse was lifted with tweezers, a small open was made by cutting, then incision was made by cutting from both sides to the back of mouse, and the skin was teared up and down with large tweezers to fully expose the abdomen. The peritoneum was lifted with sterile ophthalmic forceps, a small slit was made in the center of the peritoneum, and then a 1 mL pipette was used to take out all the ascites in the abdominal cavity through the small slit. The collected ascites could be mixed and centrifuged in a centrifuge tube at 3000 rpm for 20 min. The supernatant was collected after centrifugation.

2.4 Purification of monoclonal antibody ascites

The purified monoclonal antibody was obtained by ammonium sulfate precipitation and purification by Protein A affinity chromatography (purchased from GE, USA).

The following monoclonal antibodies were obtained by the above method: 1B11, 2A7, 6E1, 14C6, 18B2-2, 14C7, 5H4, 1F9. Among them, the obtained hybridoma cell lines 2A7 and 18B2-2 were deposited as described above in the China Center for Type Culture Collection (CCTCC).

Example 3: In Vitro Epitope Identification of Anti-HBcAg Mouse Monoclonal Antibody 3.1 Peptide synthesis Using the HBV sequence GenBank ID: CAA59669.1 as the reference sequence, 31 polypeptides were synthesized (entrusted to Shanghai Sangon Biotechnology Co., Ltd.). These 31 polypeptides (s1 to s31) together covered the full-length 183 amino acids of HBcAg. The polypeptide information of S1 to S31 was shown in Table 1 below, and the full-length amino acid sequence of HBcAg was set forth in GenBank: GU357842.1.

TABLE 1

| Peptide information of S1 to S31 | | | |
|---|---|---|---|
| Name | Amino acid position | Amino acid sequence | SEQ ID NO: |
| S1 | HBcAg-aa1-aa15 | MDIDPYKEFGATVEL | 18 |
| S2 | HBcAg-aa6-aa20 | YKEFGATVELLSFLP | 19 |
| S3 | HBcAg-aa11-aa25 | ATVELLSFLPSDFFP | 20 |
| S4 | HBcAg-aa16-aa30 | LSFLPSDFFPSIRDL | 21 |
| S5 | HBcAg-aa21-aa35 | SDFFPSVRDLLDTAS | 22 |
| S6 | HBcAg-aa26-aa40 | SVRDLLDTASALYRE | 23 |
| S7 | HBcAg-aa31-aa45 | LDTASALYREALESP | 24 |
| S8 | HBcAg-aa36-aa50 | ALYREALESPEHCSP | 25 |
| S9 | HBcAg-aa41-aa55 | ALESPEHCSPHHTAL | 26 |
| S10 | HBcAg-aa46-aa60 | EHCSPHHTALRQAIL | 27 |
| S11 | HBcAg-aa51-aa65 | HHTALRQAILCWGEL | 28 |
| S12 | HBcAg-aa56-aa70 | RQAILCWGELMNLAT | 29 |
| S13 | HBcAg-aa61-aa75 | CWGELMTLATWVGVN | 30 |
| S14 | HBcAg-aa66-aa80 | MTLATWVGVNLEDPA | 31 |
| S15 | HBcAg-aa71-aa85 | WVGVNLEDPASRDLV | 32 |
| S16 | HBcAg-aa76-aa90 | LEDPASRDLVVSYVN | 33 |
| S17 | HBcAg-aa81-aa95 | SRDLVVSYVNTNMGL | 34 |
| S18 | HBcAg-aa86-aa100 | VSYVNTNMGLKFRQL | 35 |
| S19 | HBcAg-aa91-aa105 | TNMGLKFRQLLWFHI | 36 |
| S20 | HBcAg-aa96-aa110 | KFRQLLWFHISCLTF | 37 |

TABLE 1-continued

| | Peptide information of S1 to S31 | | |
|---|---|---|---|
| Name | Amino acid position | Amino acid sequence | SEQ ID NO: |
| S21 | HBcAg-aa101-aa115 | LWFHISCLTFGRETV | 38 |
| S22 | HBcAg-aa106-aa120 | SCLTFGRETVIEYLV | 39 |
| S23 | HBcAg-aa111-aa125 | GRETVIEYLVSFGVW | 40 |
| S24 | HBcAg-aa116-aa130 | IEYLVSFGVWIRTPP | 41 |
| S25 | HBcAg-aa121-aa135 | SFGVWIRTPPAYRPP | 42 |
| S26 | HBcAg-aa126-aa140 | IRTPPAYRPPNAPIL | 43 |
| S27 | HBcAg-aa131-aa145 | AYRPPNAPILSTLPE | 44 |
| S28 | HBcAg-aa136-aa150 | NAPILSTLPETTVVR | 45 |
| S29 | HBcAg-aa141-aa154 | STLPETTVVRRRGR | 46 |
| S30 | HBcAg-aa141-aa152 | STLPETTVVRRR | 47 |
| S31 | HBcAg-aa150-aa183 | RRRGRSPRRRTPSPRRR RSQSPRRRRSQSRESQC | 48 |

3.2 Analysis of reactivity of anti-HBcAg mouse mono-clonal antibody with polypeptides S1 to S31

3.2.1 Preparation of reaction plate

The polypeptide was diluted with 50 mM CB buffer ($NaHCO_3/Na_2CO_3$ buffer, final concentration 50 mM, pH 9.6) at pH 9.6 to a final concentration of 5 µg/mL; 100 µL of coating solution was added to each well of a 96-well ELISA plate, the coating was performed at 2-8° C. for 16-24 hours and then at 37° C. for 2 hours; washing was performed once with PBST washing solution (20 mM PB7.4, 150 mM NaCl, 0.1% Tween20); then 200 µL of blocking solution (20 mM $Na_2HPO_4/NaH_2PO_4$ buffer solution containing 20% calf serum and 1% casein with pH 7.4) was added to each well, allowed to stand at 37° C. for blocking for 2 hours; the blocking solution was discarded. After drying, it was stored in aluminum foil bag at 2-8° C. for later use.

3.2.2 ELISA detection of anti-HBcAg mouse monoclonal antibody

The anti-HBcAg mouse monoclonal antibody obtained in 2.1 was diluted to 1 µg/mL with PBS solution containing 20% newborn bovine serum for qualitative ELISA detection.

Sample reaction: 36 ELISA plates that had been coated with polypeptides were taken, added with 100 µL of diluted sample to each well, and placed in an incubator to react at 37° C. for 30 minutes.

Enzyme label reaction: After the sample reaction step was completed, the ELISA plate was washed 5 times with PBST wash solution (20 mM PB7.4, 150 mM NaCl, 0.1% Tween20), and 100 µL reaction solution of HRP-labeled goat-anti-mouse IgG (GAM) was added to each well, and placed in an incubator to react at 37° C. for 30 minutes.

Color development reaction: After the enzyme label reaction step was completed, the ELISA plate was washed 5 times with PBST wash solution (20 mM PB7.4, 150 mM NaCl, 0.1% Tween20), and 50 µL of TMB color developer (purchased from Beijing Wantai Bio-pharmaceutical Co., Ltd.) was added to each well, and placed in an incubator to react at 37° C. for 15 minutes.

Termination of reaction and measurement of reading value: After the color development reaction step was completed, 50 µL of stop solution (purchased from Beijing Wantai Bio-Pharmaceutical Co., Ltd.) was added to each well of the ELISA plate, and the OD450/630 values of each well were measured by a microplate reader.

Judgment of the reactivity of anti-HBcAg mouse monoclonal antibody with 36 kinds of polypeptides: The judgment was performed according to the reading values after the reaction. If the ratio of measured value/background value was greater than 5, it was judged as positive.

3.2.3 Analysis of recognition properties of anti-HBcAg mouse monoclonal antibody The results were shown in Table 2. The recognition types of the obtained anti-HBcAg mouse monoclonal antibodies could be divided into 5 groups (according to their recognition properties), namely: sA, sB, sC, sD, sE, among which the polypeptides recognized by the sA group antibodies were S29/530, in which 2A7, 14C6, and 14C7 belonged to the sA group; the polypeptides recognized by the sB group antibodies were 531, in which 1F9 and 18B2-2 belonged to the sB group; the polypeptides recognized by the sC group antibodies were S1; the polypeptides recognized by the sD group antibodies were s26, s27; and the polypeptides recognized by the sE group antibodies were s15 and s16.

TABLE 2

| | Analysis of recognition properties of monoclonal antibodies | | |
|---|---|---|---|
| Group | Name of monoclonal antibody | Isotype of monoclonal antibody | polypeptides recognized |
| sA | HBc-2A7 | IgG2B | S29/S30 |
| sA | HBc-14C6 | IgG1 | S29/S30 |
| sC | HBc-5H4 | IgG1 | S1 |
| sA | HBc-14C7 | IgG1 | S29/S30 |
| sB | HBc-18B2-2 | IgG1 | S31 |
| sD | HBc-1B11 | IgG1 | S26/S27 |
| sE | HBc-6E1 | IgG2A | S15/S16 |
| sB | HBc-1F9 | IgG2B | S31 |

The detection results of antibodies 2A7, 18B2-2 with the corresponding epitopes were shown in Table 3, which showed that the epitope of 2A7 was in 141-152aa, and the epitope of 18B2-2 was in 150-183aa.

TABLE 3

| | Reaction of 2A7/18B2-2 with specific epitopes | | |
|---|---|---|---|
| Group | Name of monoclonal antibody | polypeptides recognized | Reaction, OD450 (1 ug/ml) |
| sA | 2A7 | S30 | 2.111 |
| sB | 18B2-2 | s31 | 2.220 |

Example 4: Epitope Identification In Vivo 4.1 Eukaryotic plasmid construction

The sequences in the fragment with a total of 222 amino acids consisting of HBcAg sequence of HBV gene and the sequence from −29 to −1 at its N-terminal were constructed into the downstream of CMV promoter in eukaryotic expression vector (EHRP vector, obtained from National Research Center of Infectious Disease Diagnostic Reagent and Vaccine Engineering Technology Research Center of Xiamen University), and the schematic diagram of its structure was shown in FIG. 1, in which C149 to C183 referred to the HBcAg sequences (starting from the +1 position) truncated from the C-terminus to the amino acid positions corresponding to the numbers respectively, pca-C183 referred to −29 to 183 fragment, pcb-C183 referred to –20 to 183 fragment, and pcc-C183 referred to –10 to 183 fragment.

4.2 Eukaryotic expression and western blot evaluation

293β5 cells were placed in a 6-well plate, and when the cell density reached about 80-90% after 12 hours of adherence, transfection was performed, the constructed eukaryotic expression plasmids were transfected into 293β5 cells using lipo3000 transfection reagent. The replacement with medium (DMEM+10% Gibco FBS) was performed 12 hours after the transfection, the culture was continued for 48 h. The cell supernatant was discarded, the cells was washed once with PBS, 300 μL of cell lysis solution was added to each well and allowed to stand at 4° C. for 1 h to perform lysis. The lysate was collected in a 1.5 ml EP tube, centrifuged at 12000 rpm at 4° C. for 10 min, the supernatant was collected into a clean 1.5 ml EP tube, and the lysed sample was subjected to western blot analysis (the secondary antibody was goat-anti-mouse-HRP, purchased from proteintec company).

4.3 Analysis of results

Figure 2:
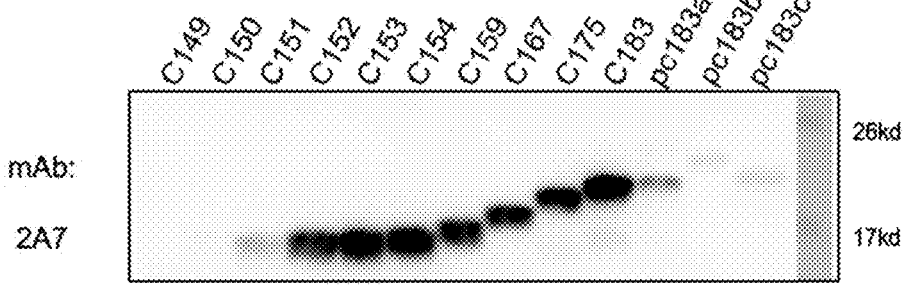
FIG. 2 shows the results of western blot analysis of HBV antigens of different lengths by using 2A7 as the primary antibody.

The monoclonal antibodies were evaluated using antigens of different lengths constructed by in vivo eukaryotic expression, and the results were shown in FIG. 2. The results verified that the recognition site of 2A7-21 was 141-152aa.

Example 5: Screening of Magnetic Bead-Coated Monoclonal Antibody and Acridinium Ester-Labeled Monoclonal Antibody in Double Antibody-Sandwich Method In this example, the experimental conditions of conventional double antibody-sandwich method were adopted to screen the optimal pairing of the monoclonal antibody for coating magnetic bead and the monoclonal antibody for labeling with acridinium ester.

5.1 Preparation of HBcAg magnetic bead-coated monoclonal antibody

The magnetic microparticle solution was prepared, and the magnetic microparticles were magnetic beads coated with hydrophilic polymers and carboxyl groups on the surface with the particle size of 1.5-3 um. The preparation method was as follows: magnetic microparticles, EDC and NHS at the mass ratio of 1:1:1 were added with 50 mM MES solution with pH 5.0 to make the concentration of magnetic microparticles to be 4 mg/mL. It was then loaded on a vertical rotator for activation at environmental temperature of 25° C. for 20 minutes. The activated magnetic microparticles and the anti-HBcAg monoclonal antibody at a ratio of 15 μg of anti-HBcAg monoclonal antibody per mg of magnetic microparticles were loaded on a vertical rotator for labeling, and the reaction was performed at environmental temperature of 25° C. for 3 h. The magnetic microparticles after the reaction were washed 3 times with washing solution, then a phosphate buffer at pH 7.4 containing glycine, 0.5% bovine serum albumin and 0.05% Triton X-100 were added to make the magnetic microparticles to have a concentration of 4 mg/mL, and loaded on the vertical rotator for termination at the reaction temperature of 25° C. for 2 h. The magnetic microparticles after the termination were washed 3 times with washing solution, and a phosphate buffer at pH 7.4 containing 0.5% (W/V) bovine serum albumin, 0.5% (W/V) casein, 0.05% (W/V) Triton X-100, and preservative was added to make the magnetic microparticles to have a concentration of 4 mg/mL, and was stored at 2-8° C. for later use.

The monoclonal antibodies (18B2-2, 1F9) recognizing aa150-183 were coated with MS300 magnetic beads according to the above-mentioned method to prepare magnetic microparticle solutions.

5.2 Preparation of HBcAg acridinium ester-labeled monoclonal antibody

The acridinium ester-labeled antibody solution was prepared, and the preparation method was as follows: 50 ug of the anti-HBcAg monoclonal antibody to be labeled was added with NaCl-containing phosphate buffer to reach a volume of 300 μL, then 5 μL of acridinium ester stock solution was added, shaken and mixed, and the reaction was performed in the dark at room temperature for 30 min; after the reaction, 200 μL of a phosphate buffer containing NaCl and glycine was added, mixed by manually turning upside down for 20 times, and the reaction was performed at room temperature for 30 min in the dark; after the reaction, the product was transferred into a dialysis bag, and dialyzed in the dark at 2-8° C. against a dialysate that was 20 mM PBS buffer at pH 7.4, the PBS buffer was changed every 2 h for a total of 3 times to remove the unlabeled acridinium ester; the labeled product was added with 10% (W/V) bovine serum albumin according to the actual volume so that the bovine serum albumin had a final concentration of 0.1% (V/V, 1:100), then added with an equal volume of glycerol, mixed by manually turning upside down, and stored at –15° C. in the dark for later use.

Six HBcAg monoclonal antibodies (1B11, 2A7, 6E1, 14C6, 14C7, 5H4) were labeled with acridinium ester by the above-mentioned method.

5.3 Experimental method 5.3.1 Samples:

HBV virus positive (PCR detection) clinical serum sample was provided, and diluted with 20% NBS to reach different DNA loads of $1*10^7$, $1*10^6$, $1*10^5$, $1*10^4$, $1*10^3$ to obtain positive samples for detection; and HBV virus negative (PCR detection) clinical serum sample was also provided.

5.3.2 Loading sample:

25 ul sample was added with 12.5 ul of 20% LDS, mixed and then incubated at 37° C. for 30 min. 30 ul of 10% CHAPS was added and mixed to neutralize, then 50 ul of magnetic bead-coated monoclonal antibody was added and incubated at 37° C. for 15 min. After the incubation was completed, washing was performed with a phosphate buffer containing 0.05~0.08% Tween 20, then 50 ul of acridinium ester-labeled monoclonal antibody was added, shaken and mixed, incubated at 37° C. for 10 min. After incubation, washing was performed with a phosphate buffer containing 0.05~0.08% Tween 20, and 100~200 ul of pre-trigger solution was added to perform pre-trigger. After the pre-trigger solution was removed, 100~200 ul of trigger solution was added to perform trigger and detection.

The orthogonal detection of each magnetic bead-coated monoclonal antibody paired with each acridinium ester-labeled monoclonal antibody was performed by the above-mentioned method, and the P/N (ratio of the mean value of positive sample to the mean value of negative sample) was calculated. The results were shown in the table below.

TABLE 4-1

P/N values of pairing detection of magnetic bead-coated monoclonal antibody 18B2-2
and acridinium ester-labeled monoclonal antibody

| | Coated-antibody (18B2-2) | | | | | | | | | | |
|---|---|---|---|---|---|---|---|---|---|---|---|
| | Positive sample $(1*10^7)$ | | Positive sample $(1*10^6)$ | | Positive sample $(1*10^5)$ | | Positive sample $(1*10^4)$ | | Positive sample $(1*10^3)$ | | Negative sample |
| Labeled antibody | RLU | P/N | RLU | P/N | RLU | P/N | RLU | P/N | RLU | P/N | RLU |
| 1B11 | 8692 | 16.9 | 2563 | 5.0 | 1660 | 3.2 | 520 | 1.0 | 504 | 1.0 | 515 |
| 5H4 | 7849 | 10.2 | 3918 | 5.1 | 1759 | 2.3 | 684 | 0.9 | 601 | 0.8 | 773 |
| 6E1 | 45203 | 20.1 | 12266 | 5.4 | 8256 | 3.7 | 3316 | 1.5 | 2549 | 1.1 | 2253 |
| 14C6 | 129622 | 140.1 | 45445 | 49.1 | 11281 | 12.2 | 4830 | 5.2 | 1595 | 1.7 | 925 |
| 14C7 | 153900 | 165.3 | 54505 | 58.5 | 12296 | 13.2 | 5882 | 6.3 | 2468 | 2.7 | 931 |
| 2A7 | 649026 | 318.7 | 173474 | 85.2 | 54199 | 26.6 | 17853 | 8.8 | 6981 | 3.4 | 2037 |

TABLE 4-2

P/N values of pairing detection of magnetic bead-coated monoclonal antibody 1F9 and
acridinium ester-labeled monoclonal antibody

| | Coated-antibody (1F9) | | | | | | | | | | |
|---|---|---|---|---|---|---|---|---|---|---|---|
| | Positive sample $(1*10^7)$ | | Positive sample $(1*10^6)$ | | Positive sample $(1*10^5)$ | | Positive sample $(1*10^4)$ | | Positive sample $(1*10^3)$ | | Negative sample |
| Labeled antibody | RLU | P/N | RLU | P/N | RLU | P/N | RLU | P/N | RLU | P/N | RLU |
| 1B11 | 1566 | 13.86 | 773 | 6.84 | 263 | 2.33 | 166 | 1.47 | 164 | 1.45 | 113 |
| 5H4 | 2279 | 11.23 | 857 | 4.22 | 531 | 2.62 | 268 | 1.32 | 306 | 1.51 | 203 |
| 6E1 | 1910 | 13.26 | 658 | 4.57 | 183 | 1.27 | 174 | 1.21 | 200 | 1.39 | 144 |
| 14C6 | 24910 | 54.99 | 8443 | 18.64 | 3630 | 8.01 | 1457 | 3.22 | 357 | 0.79 | 453 |
| 14C7 | 29077 | 118.20 | 8357 | 33.97 | 2355 | 9.57 | 1452 | 5.90 | 340 | 1.38 | 246 |
| 2A7 | 94536 | 243.65 | 18329 | 47.24 | 4353 | 11.22 | 2164 | 5.58 | 1435 | 3.70 | 388 |

Tables 4-1 and 4-2 showed the detection results of samples with different DNA loads (P/N>3 represented positive) by using the antibody that recognized HBcAg aa150-183 (i.e., recognized the Arginine Rich Domain (ARD) of HBcAg) to coat magnetic beads and using the monoclonal antibodies that recognized different epitopes in 1-149aa of HBcAg as labeling antibodies. The results showed that when the three antibodies (2A7, 14C6, 14C7) that recognized the HBcAg 141-154aa epitope were used as the labeling antibodies, the detection effect of the samples with different HBV DNA loads was significantly better than that of other antibody pairs.

Example 6: Enzyme Immunoassay and Detection Reagent for Detecting HBcAg

The monoclonal antibody 18B2-2 was diluted with phosphate buffer (20 mmol/LPB, pH 7.4) and coated on a polyvinyl chloride plate, and the monoclonal antibody 2A7 was labeled with horseradish peroxidase (Beijing Wantai Bio-pharmaceuticals, Co., Ltd.). The samples to be tested included: C183 antigen dilution with a concentration of 1 ug/ml, C149 antigen (developed by the Laboratory of National Infectious Disease Diagnostic Reagent and Vaccine Engineering Technology Research Center of Xiamen University) dilution with a concentration of 1 µg/ml, positive sample 1/2, negative sample 1/2, and 20% nbs.

Figure 3:
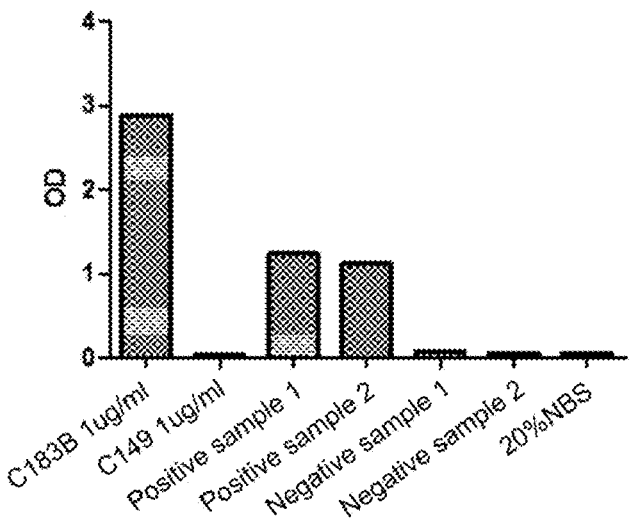
FIG. 3 shows the detection results of HBcAg in different samples by the enzyme immunoassay of the invention.

The samples were treated with the same method as in Example 5 to lysis viruses. Subsequently, 2A7-HRP (1/500 dilution) was added and incubated for 40 min, the plate was washed 5 times, and 50 ul each of chromogenic solution A and B (Beijing Wantai Bio-Pharmaceutical Co., Ltd.) was added and incubated for 15 min. Finally, the stop solution (2M $H_2SO_4$) was added, shaken gently and mixed well, and the value at the wavelength of 450-620 was read on a microplate reader. The results were shown in FIG. 3, the enzyme immunoassay detection reagent of the invention could specifically detect HBcAg, but did not detect c149 (i.e., HBeAg), indicating that it had good specificity.

Example 7: Chemiluminescence Detection Method and Reagent for Detecting HBcAg 7.1 Preparation of detection kit
7.1.1 Preparation of magnetic bead-coated monoclonal antibody
The magnetic microparticles were magnetic beads coated with hydrophilic polymers and carboxyl groups on the surface with the particle size of 1.5-3 um. The preparation method thereof was as follows: the magnetic microparticles, EDC and NHS in a mass ratio of 1:1:1 were added with 50 mM MES solution at pH 5.0 to make the magnetic microparticles to have a concentration of 4 mg/mL, then loaded on a vertical rotator for activation at environmental temperature of 25° C. for 20 min. The activated magnetic microparticles and the 18B2-2 monoclonal antibody at a ratio of 15 ug of HBcAg monoclonal antibody per mg of magnetic microparticles were loaded on a vertical rotator for labeling, and the reaction was performed at an environmental temperature of 25° C. for 3 hours. The reacted magnetic microparticles were washed three times with washing solution, added with a phosphate buffer at pH 7.4 containing glycine, 0.5% bovine serum albumin, 0.05% Triton X-100 to make the magnetic particles to have a concentration of 4 mg/mL, loaded on a vertical rotator to perform termination at a reaction environment temperature of 25° C. for 2 h. The magnetic particles after the termination were washed 3 times with washing solution, added with a phosphate buffer at pH 7.4 containing 0.5% (w/v) bovine serum albumin, 0.5% (w/v) casein, 0.05% (w/v) Triton X-100, and preservative to make the magnetic microparticles to have a concentration of 4 mg/mL, and stored at 2-8° C. for later use.

7.1.2 Preparation of acridinium ester-labeled monoclonal antibody

The preparation method was as follows: 50 ug of the 2A7 monoclonal antibody to be labeled was added with a phosphate buffer containing NaCl to reach a volume of 300 μL, then added with 5 μL of acridinium ester stock solution, shaken and mixed well, and the reaction was performed at room temperature for 30 min in the dark. After the reaction, 200 μL of a phosphate buffer containing NaCl and glycine was added, mixed by manually turning upside down for 20 times, and the reaction was performed at room temperature for 30 min in the dark. After the reaction, the product was transferred to a dialysis bag, and dialyzed at 2-8° C. in the dark against a dialysate that was 20 mM PBS buffer at pH 7.4, the PBS buffer was changed every 2 h for a total of 3 times to remove the unlabeled acridinium ester. The labeled product was added with 10% (W/V) bovine serum albumin according to the actual volume so that the bovine serum albumin had a final concentration of 0.1% (V/V, 1:100), and added with an equal volume of glycerol, mixed by manually turning upside-down and stored at −15° C. in the dark for later use.

7.2 Detection method

1. Preparation: The kit obtained in 7.1 was allowed to stand and equilibrate at room temperature (18-30° C.) for 15-30 min.
2. Liquid preparation: 50 ml of concentrated washing solution (20×) was diluted with distilled water or deionized water to 1000 ml for later use.
3. Adding sample: 25 ul of samples to be tested were added to the corresponding wells respectively.
4. Lysis: The same method as described in Example 5 was adopted to lyse viruses.
5. Reaction: 50 ul of magnetic bead-coated monoclonal antibody 18B2-2 was added to the sample well; after being mixed well, the plate was sealed with sealing film, and incubated at 37±1° C. for 15 min. After the incubation for 15~20 min, washing was performed with a phosphate buffer containing 0.05~0.08% Tween 20, then 50 ul of acridinium ester-labeled antibody 2A7 was added, and incubated for 10~15 min. After incubation, washing was performed with a phosphate buffer containing 0.05~0.08% Tween 20, then 100~200 ul of pre-trigger solution was added to perform pre-trigger. Then, the pre-trigger solution was removed, and 100~200 ul of trigger solution was added to perform trigger and detection.

Result Judgment

Threshold: Cut Off (C.O.)=9000

Result Judgment: (S=Luminescence Value of Each Well)

Negative result: (S/C.O.<1): Negative was determined when the luminescence value of the sample was less than the Cut Off value, which meant that the HBV core antigen was not detected in the sample.

Positive result: (S/C.O.≥1): Positive was determined when the luminescence value of the sample was greater than or equal to the Cut Off value, which meant that the HBV core antigen was detected in the sample.

Example 8: Specificity and Sensitivity Analysis of HBcAg Detection Kit 8.1 Specificity analysis of core antigen detection kit 8.1.1 Preparation of kit The luminescence diagnostic kit (luminescence detection reagent method) for detecting HBV core antigen was prepared according to the method as described in Example 7.

8.1.2 Detection of samples

A total of 80 samples collected from April 2019 to the present, which had negative results in all the items of HBsAg, HBsAb, HBeAg, HBeAb and HBcAb5 of Hepatitis B serologic test, were cryopreserved at −20° C.

8.1.3 Detection items

Each of the serum samples was subjected to chemiluminescence detection for hepatitis B virus core antigen, and the method was shown in Example 7.

8.1.4 Detection results

After all samples were detected, the results were analyzed for the specificity of the kit. The detection results of each sample were shown in the table below.

TABLE 7

| Detection results | | |
|---|---|---|
| Sample No. | RLU | S/C.O. |
| 1 | 4042 | 0.45 |
| 2 | 7762 | 0.86 |
| 3 | 2415 | 0.27 |
| 4 | 3289 | 0.37 |
| 5 | 3934 | 0.44 |
| 6 | 2659 | 0.30 |
| 7 | 4208 | 0.47 |
| 8 | 3353 | 0.37 |
| 9 | 5665 | 0.63 |
| 10 | 5729 | 0.64 |
| 11 | 6535 | 0.73 |
| 12 | 4042 | 0.45 |
| 13 | 4074 | 0.45 |
| 14 | 4845 | 0.54 |
| 15 | 7663 | 0.85 |
| 16 | 7635 | 0.85 |
| 17 | 3915 | 0.44 |
| 18 | 3263 | 0.36 |
| 19 | 3359 | 0.37 |
| 20 | 4642 | 0.52 |
| 21 | 6425 | 0.71 |
| 22 | 2001 | 0.22 |
| 23 | 6185 | 0.69 |
| 24 | 6711 | 0.75 |
| 25 | 4260 | 0.47 |
| 26 | 3622 | 0.40 |
| 27 | 2002 | 0.22 |
| 28 | 6600 | 0.73 |
| 29 | 3373 | 0.37 |
| 30 | 3506 | 0.39 |
| 31 | 4236 | 0.47 |
| 32 | 5977 | 0.66 |
| 33 | 2003 | 0.22 |
| 34 | 4441 | 0.49 |
| 35 | 5622 | 0.62 |
| 36 | 3348 | 0.37 |
| 37 | 2247 | 0.25 |
| 38 | 5231 | 0.58 |
| 39 | 2703 | 0.30 |
| 40 | 4687 | 0.52 |
| 41 | 4250 | 0.47 |
| 42 | 7862 | 0.87 |
| 43 | 7690 | 0.85 |
| 44 | 4921 | 0.55 |
| 45 | 5134 | 0.57 |

TABLE 7-continued

| Detection results | | |
|---|---|---|
| Sample No. | RLU | S/C.O. |
| 46 | 2610 | 0.29 |
| 47 | 2011 | 0.22 |
| 48 | 4551 | 0.51 |
| 49 | 7942 | 0.88 |
| 50 | 4328 | 0.48 |
| 51 | 3660 | 0.41 |
| 52 | 3398 | 0.38 |
| 53 | 4108 | 0.46 |
| 54 | 6807 | 0.76 |
| 55 | 4818 | 0.54 |
| 56 | 4525 | 0.50 |
| 57 | 3793 | 0.42 |
| 58 | 5096 | 0.57 |
| 59 | 4639 | 0.52 |
| 60 | 4899 | 0.54 |
| 61 | 4482 | 0.50 |
| 62 | 5347 | 0.59 |
| 63 | 7227 | 0.80 |
| 64 | 5773 | 0.64 |
| 65 | 4618 | 0.51 |
| 66 | 6705 | 0.75 |
| 67 | 5271 | 0.59 |
| 68 | 3337 | 0.37 |
| 69 | 5560 | 0.62 |
| 70 | 4115 | 0.46 |
| 71 | 6320 | 0.70 |
| 72 | 5610 | 0.62 |
| 73 | 4806 | 0.53 |
| 74 | 3181 | 0.35 |
| 75 | 7675 | 0.85 |
| 76 | 6643 | 0.74 |
| 77 | 4273 | 0.47 |
| 78 | 6221 | 0.69 |
| 79 | 6740 | 0.75 |
| 80 | 6391 | 0.71 |

8.1.5 Results and analysis

It could be seen from the results in Table 7 that S/C.O.<1 indicated that the HBV core antigen was not detected in the sample, and the specificity was good.

8.2 Sensitivity analysis of core antigen detection kit 8.2.1 Preparation of kit

The luminescence diagnostic kit for detecting HBV core antigen (by luminescence detection reagent method) was prepared according to the method as described in Example 7.

8.2.2 Detection of samples 8.2.2.1. One fresh serum sample with a DNA load of 1.60E+08 copies/mL detected by hepatitis B virus nucleic acid quantitative PCR detection reagent was subjected to linear dilution with 20% NBS at 11 points with 3-fold gradient, and 20% NBS was used as a negative control; the detection was carried out according to the method described in Example 8, and a reference curve was made.

8.2.2.2. The C183B antigen was diluted with 20% NBS to 1 μg/ml, and subjected to dilution at 11 points with 3-fold gradient, and 20% NBS without C183B antigen was used as a negative control; the detection was carried out according to the method described in Example 8, and the above reference curve was used to convert the value corresponding to the antigen detection at each point. The results were shown in the table below.

TABLE 8

| Detection results | | | | | |
|---|---|---|---|---|---|
| C183B ng/ml | RLU1 | S/C.O. | DNA load | RLU2 | S/C.O. |
| 1000.00 | 10272307 | 1141.37 | 5.19E+08 | 1233807 | 137.09 |
| 333.33 | 3047322 | 338.59 | 1.73E+08 | 906003 | 100.67 |
| 111.11 | 1297299 | 144.14 | 5.77E+07 | 389994 | 43.33 |
| 37.04 | 459415 | 51.05 | 1.92E+07 | 164105 | 18.23 |
| 12.35 | 177478 | 19.72 | 6.41E+06 | 64594 | 7.18 |
| 4.12 | 85184 | 9.46 | 2.14E+06 | 25633 | 2.85 |
| 1.37 | 39003 | 4.33 | 7.12E+05 | 14108 | 1.57 |
| 0.46 | 19941 | 2.22 | 2.37E+05 | 10453 | 1.16 |
| 0.15 | 11277 | 1.25 | 7.91E+04 | 9244 | 1.03 |
| 0.05 | 9368 | 1.04 | 2.64E+04 | 6975 | 0.78 |
| 0.02 | 6532 | 0.73 | 8.79E+03 | 3558 | 0.40 |
| 20% nbs | 2780 | 0.31 | 20% nbs | 2195 | 0.24 |

8.2.2.3. Results and analysis

In the data of Table 8, S/C.O greater than 1 represented positive, while less than 1 represented negative. The results showed that the antigen detection sensitivity of c183 was 0.05 ng/ml, and the sample detection sensitivity was about $10^4$ copies/ml (DNA load).

Example 9: Comparison of HBcAg Detection Kit and PCR Detection Method 9.1 Preparation of kit 9.1.1 The luminescence diagnostic kit for detecting HBV core antigen (by luminescence detection reagent method) was prepared according to the method described in Example 7.

9.1.2 The hepatitis B virus nucleic acid quantitative PCR detection reagents were purchased from Shenzhen Piji Bio-engineering Co., Ltd.

9.2 Detection samples

A total of 82 hepatitis B virus-infected serum samples collected since April 2019 to the present were cryopreserved at −20° C.

9.3 Detection items

Quantitative PCR detection of hepatitis B virus nucleic acid was performed on each serum sample.

Chemiluminescence detection of hepatitis B virus core antigen was performed on each serum sample.

9.4 Detection results

The correlation between HBV core antigen detection and HBV virus nucleic acid detection was analyzed by comparing the detection results of all items. The results were shown in the table below.

TABLE 9

| Detection results of HBsAg-positive hepatitis B virus-infected serum samples | | | | | |
|---|---|---|---|---|---|
| Sample No. | DNA load | Lg(DNA load) | RLU | S/C.O. | Lg(RLU) |
| 1 | 5.22E+02 | 2.72 | 7058 | 0.78 | 3.85 |
| 2 | 5.54E+02 | 2.74 | 9611 | 1.07 | 3.98 |
| 3 | 8.61E+02 | 2.94 | 5454 | 0.61 | 3.74 |
| 4 | 9.35E+02 | 2.97 | 7074 | 0.79 | 3.85 |
| 5 | 1.10E+03 | 3.04 | 7360 | 0.82 | 3.87 |
| 6 | 1.22E+03 | 3.09 | 7795 | 0.87 | 3.89 |
| 7 | 1.57E+03 | 3.20 | 6627 | 0.74 | 3.82 |
| 8 | 1.65E+03 | 3.22 | 8167 | 0.91 | 3.91 |
| 9 | 2.40E+03 | 3.38 | 6574 | 0.73 | 3.82 |
| 10 | 2.68E+03 | 3.43 | 5818 | 0.65 | 3.76 |
| 11 | 2.85E+03 | 3.45 | 8450 | 0.94 | 3.93 |
| 12 | 3.23E+03 | 3.51 | 9279 | 1.03 | 3.97 |
| 13 | 1.33E+04 | 4.12 | 9822 | 1.09 | 3.99 |
| 14 | 1.53E+04 | 4.18 | 11797 | 1.31 | 4.07 |
| 15 | 1.57E+04 | 4.20 | 11252 | 1.25 | 4.05 |
| 16 | 3.03E+04 | 4.48 | 18600 | 2.07 | 4.27 |
| 17 | 4.24E+04 | 4.63 | 11099 | 1.23 | 4.05 |

TABLE 9-continued

Detection results of HBsAg-positive hepatitis B virus-infected
serum samples

| Sample No. | DNA load | Lg(DNA load) | RLU | S/C.O. | Lg(RLU) |
|---|---|---|---|---|---|
| 18 | 6.94E+04 | 4.84 | 13330 | 1.48 | 4.12 |
| 19 | 2.08E+05 | 5.32 | 5862 | 0.65 | 3.77 |
| 20 | 2.60E+05 | 5.41 | 29362 | 3.26 | 4.47 |
| 21 | 9.62E+05 | 5.98 | 25736 | 2.86 | 4.41 |
| 22 | 1.19E+06 | 6.08 | 51702 | 5.74 | 4.71 |
| 23 | 4.93E+06 | 6.69 | 17820 | 1.98 | 4.25 |
| 24 | 2.11E+07 | 7.32 | 99756 | 11.08 | 5.00 |
| 25 | 2.68E+07 | 7.43 | 283919 | 31.55 | 5.45 |
| 26 | 3.47E+07 | 7.54 | 152230 | 16.91 | 5.18 |
| 27 | 3.74E+07 | 7.57 | 1067414 | 118.60 | 6.03 |
| 28 | 4.79E+07 | 7.68 | 455741 | 50.64 | 5.66 |
| 29 | 1.01E+08 | 8.00 | 1434375 | 159.38 | 6.16 |
| 30 | 1.05E+08 | 8.02 | 74442 | 8.27 | 4.87 |
| 31 | 1.26E+08 | 8.10 | 160285 | 17.81 | 5.20 |
| 32 | 1.48E+08 | 8.17 | 1017496 | 113.06 | 6.01 |
| 33 | 1.54E+08 | 8.19 | 205803 | 22.87 | 5.31 |
| 34 | 1.64E+08 | 8.21 | 252638 | 28.07 | 5.40 |
| 35 | 3.28E+08 | 8.52 | 1503273 | 167.03 | 6.18 |
| 36 | 5.38E+08 | 8.73 | 2669259 | 296.58 | 6.43 |
| 37 | 1.15E+03 | 3.06 | 9936 | 1.10 | 4.00 |
| 38 | 9.14E+07 | 7.96 | 170179 | 18.91 | 5.23 |
| 39 | 1.26E+08 | 8.10 | 940798 | 104.53 | 5.97 |
| 40 | 5.39E+07 | 7.73 | 110586 | 12.29 | 5.04 |
| 41 | 9.02E+07 | 7.96 | 124868 | 13.87 | 5.10 |
| 42 | 1.96E+04 | 4.29 | 10500 | 1.17 | 4.02 |
| 43 | 2.04E+03 | 3.31 | 9001 | 1.00 | 3.95 |
| 44 | 5.19E+08 | 8.72 | 1053667 | 117.07 | 6.02 |
| 45 | 1.09E+06 | 6.04 | 14822 | 1.65 | 4.17 |
| 46 | 4.09E+04 | 4.61 | 9546 | 1.06 | 3.98 |
| 47 | 1.25E+03 | 3.10 | 4749 | 0.53 | 3.68 |
| 48 | 1.92E+03 | 3.28 | 9042 | 1.00 | 3.96 |
| 49 | 2.96E+08 | 8.47 | 810430 | 90.05 | 5.91 |
| 50 | 1.36E+08 | 8.13 | 327209 | 36.36 | 5.51 |
| 51 | 9.75E+03 | 3.99 | 7899 | 0.88 | 3.90 |
| 52 | 4.38E+03 | 3.64 | 4702 | 0.52 | 3.67 |
| 53 | 6.35E+03 | 3.80 | 9578 | 1.06 | 3.98 |
| 54 | 1.26E+05 | 5.10 | 22687 | 2.52 | 4.36 |
| 55 | 1.73E+05 | 5.24 | 16642 | 1.85 | 4.22 |
| 56 | 1.73E+05 | 5.24 | 10389 | 1.15 | 4.02 |
| 57 | 2.11E+03 | 3.32 | 8117 | 0.90 | 3.91 |
| 58 | 1.96E+03 | 3.29 | 7350 | 0.82 | 3.87 |
| 59 | 2.83E+06 | 6.45 | 22523 | 2.50 | 4.35 |
| 60 | 1.25E+03 | 3.10 | 10673 | 1.19 | 4.03 |
| 61 | 1.06E+09 | 9.03 | 1432767 | 159.20 | 6.16 |
| 62 | 9.48E+06 | 6.98 | 28928 | 3.21 | 4.46 |
| 63 | 1.35E+04 | 4.13 | 9640 | 1.07 | 3.98 |
| 64 | 1.88E+04 | 4.27 | 9524 | 1.06 | 3.98 |
| 65 | 8.82E+07 | 7.95 | 292615 | 32.51 | 5.47 |
| 66 | 8.82E+07 | 7.95 | 110758 | 12.31 | 5.04 |
| 67 | 3.29E+03 | 3.52 | 6017 | 0.67 | 3.78 |
| 68 | 7.18E+06 | 6.86 | 27373 | 3.04 | 4.44 |
| 69 | 7.75E+04 | 4.89 | 9986 | 1.11 | 4.00 |
| 70 | 3.03E+05 | 5.48 | 13518 | 1.50 | 4.13 |
| 71 | 7.43E+07 | 7.87 | 233848 | 25.98 | 5.37 |
| 72 | 3.84E+07 | 7.58 | 148066 | 16.45 | 5.17 |
| 73 | 1.33E+08 | 8.12 | 439697 | 48.86 | 5.64 |
| 74 | 2.36E+05 | 5.37 | 18871 | 2.10 | 4.28 |
| 75 | 2.72E+08 | 8.43 | 460449 | 51.16 | 5.66 |
| 76 | 3.78E+04 | 4.58 | 10103 | 1.12 | 4.00 |
| 77 | 6.50E+07 | 7.81 | 255839 | 28.43 | 5.41 |
| 78 | 7.35E+05 | 5.87 | 15580 | 1.73 | 4.19 |
| 79 | 3.57E+07 | 7.55 | 255944 | 28.44 | 5.41 |
| 80 | 8.58E+04 | 4.93 | 9963 | 1.11 | 4.00 |
| 81 | 1.50E+04 | 4.18 | 12018 | 1.34 | 4.08 |
| 82 | 4.29E+03 | 3.63 | 6577 | 0.73 | 3.82 |

9.5 Analysis of results

Figure 4:
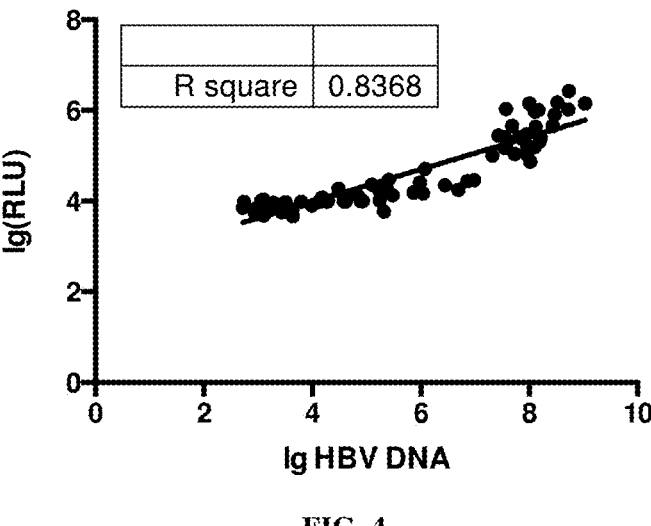
FIG. 4 shows the correlation between the results of the chemiluminescence detection method of the invention and the PCR detection.

In Table 9, S/C.O.>1 represented that the core antigen was detected in the sample, and S/C.O.<1 represented that the core antigen was not detected in the sample. Correlation analysis was carried out between the results of HBcAg detection and the DNA load results obtained by PCR method; specifically, the logarithm of the virus content and the luminescence intensity of each sample were taken and the linear correlation analysis was carried out. As shown in in FIG. 4, $R^2$ was 0.8368, this result indicated that the detection performance of the HBcAg detection method of the invention was good, and can be used to evaluate the DNA load of the sample.

Example 10: Use of 2A7 Monoclonal Antibody in Other Immunological Assays 10.1 Use of 2A7 as HBcAg immunofluorescence detection antibody HepG2 (obtained from the Laboratory of National Infectious Disease Diagnostic Reagents and Vaccine Engineering Technology Research Center, Xiamen University) and HepG2-N10 cells stably integrated with a HBV 1.1-fold genome (obtained from the Laboratory of National Infectious Disease Diagnostic Reagent and Vaccine Engineering Technology Research Center, Xiamen University) were plated in a 24-well plate with 60,000 cells per well. After 12 hours for cell adhesion, the medium was removed, washing was performed once with 20 mM PBS. After fixing with 4% paraformaldehyde for 15 min, the cells were permeabilized with 0.02% Triton x-100 for 10 min, and blocked with 2% BSA for 1 hour. And then the 2A7 monoclonal antibody (1 mg/ml) diluted by 2% BSA at a dilution ratio of 1:1000, was added and incubated at room temperature for 1 hour, and washed 4 times with PBS. The fluorescent secondary antibody, goat-anti-mouse-Alexa488 (Beyotime, Cat. No: A0428), was added and the incubation was carried out at room temperature for 40 min. After washing 4 times with PBS, DAPI Staining was performed for nucleus. After the experiment was completed, the cells were photographed with a 63× water objective with an Opera phenix laser confocal high-content imaging system.

Figure 5:
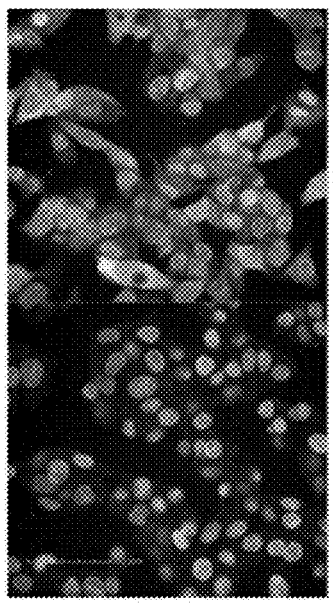
FIG. 5 shows the results of immunofluorescence detection of cell samples by using 2A7 as HBcAg immunofluorescence detection antibody.

The results were shown in FIG. 5, 2A7 had obvious immune response in cytoplasm to HepG2-N10 cells which were integrated with HBV genome, but had no binding to the cells which were not integrated with HBV genome, indicating good specificity. The above results indicated that 2A7 could be used as an immunofluorescent antibody of HBcAg for accurate detection.

10.2 Use of 2A7 as monoclonal antibody for HBcAg immunohistochemical detection

At present, the anti-HBcAg antibodies used in HBcAg immunohistochemical detection are polyclonal antibodies, but polyclonal antibodies often have high background and low specificity, and the immunohistochemical results using them are not easy to standardize. There is no report on the use of anti-HBcAg monoclonal antibody for immunohistochemical detection. In this experiment, the performance of 2A7 monoclonal antibody as an immunohistochemical detection antibody was investigated.

Hepatic tissue paraffin sections of HBV transgenic mice HBV-TG (obtained from the Laboratory of National Infectious Disease Diagnostic Reagent and Vaccine Engineering Technology Research Center, Xiamen University) and normal C57BL/6 mice (obtained from Shanghai SLAC Laboratory Animal Co., Ltd.) were subjected to dewaxing, rehydration, antigen retrieval, washing, blocking, and then added with the anti-HBc commercial polyclonal antibody and the 2A7 monoclonal antibody, for reaction at room temperature for 1 hour. After washing, a secondary antibody was added and reacted at room temperature for 10 minutes. After washing, color developing solution was added to perform staining, followed by hydrochloric acid differentiation, counterstaining, and mounting.

Figure 6:
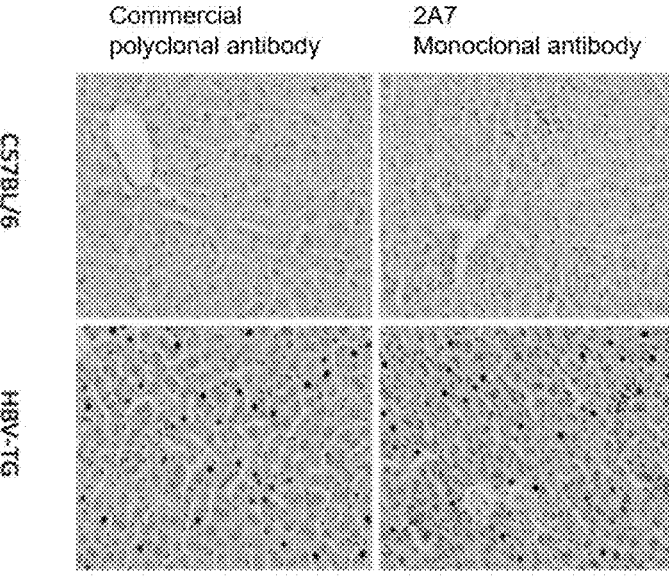
FIG. 6 shows the results of immunohistochemical detection of tissue sections by using 2A7 as HBcAg immunohistochemical detection antibody.

The results were shown in FIG. 6. Similar to the commercial polyclonal antibody, the 2A7 monoclonal antibody could accurately detect the tissue paraffin sections of HBV transgenic mice, and had no binding to the tissue paraffin sections of normal mice, indicating that the 2A7 could also be used as an immunohistochemical antibody of HBcAg for accurate detection.

Although specific embodiments of the present invention have been described in detail, those skilled in the art will appreciate that various modifications and changes can be made to the details in light of all the teachings that have been published, and that these changes are all within the scope of the present invention. The full scope of the present invention is given by the appended claims and any equivalents thereof.

What is claimed is:

1. A method for detecting the presence or level of HBcAg protein in a sample, comprising the steps of:

(1) contacting the sample with a first antibody to form an antibody-antigen complex, wherein the first antibody is selected from an antibody or antigen-binding fragment thereof that specifically binds to positions 150-183 of HBcAg protein;

(2) contacting the antibody-antigen complex with a second antibody to form an antibody-antigen-antibody complex, wherein the second antibody is selected from an antibody or antigen-binding fragment thereof that specifically binds to positions 141-154 of HBcAg protein; and (3) determining an amount of the antibody-antigen-antibody complex;

wherein the first antibody is selected from the following antibodies or antigen-binding fragments thereof:

(i) an antibody or an antigen-binding fragment thereof, which comprises: a heavy chain variable region (VH) comprising the following 3 complementarity determining regions (CDRs): HCDR1 having a sequence set forth in SEO ID NO: 3, HCDR2 having a sequence set forth in SEO ID NO: 4, and HCDR3 having a sequence set forth in SEO ID NO: 5; and, a light chain variable region (VL) comprising the following 3 complementarity determining regions (CDRs): LCDR1 having a sequence set forth in SEO ID NO: 6, LCDR2 having a sequence set forth in SEO ID NO: 7, and LCDR3 having a sequence set forth in SEO ID NO: 8; or, (ii) an antibody or an antigen-binding fragment thereof, which comprises: a heavy chain variable region (VH) comprising 3 CDRs contained in the VH set forth in SEO ID NO: 1; and a light chain variable region (VL) comprising 3 CDRs contained in the VL set forth in SEO ID NO: 2; wherein the 3 CDRs contained in the VH and the 3 CDRs contained in the VL are defined by the Kabat, Chothia or IMGT numbering system; or, (iii) an antibody or an antigen-binding fragment thereof, wherein the antibody is a monoclonal antibody produced by a hybridoma cell line 18B2-2 which is deposited in the China Center for Type Culture Collection (CCTCC) and has the deposit number of CCTCC NO. C2019303;

and wherein the second antibody is selected from the following antibody or antigen-binding fragment thereof:

(i) an antibody or an antigen-binding fragment thereof, comprising: a heavy chain variable region (VH) comprising the following 3 complementarity determining regions (CDRs): HCDR1 having a sequence set forth in SEO ID NO: 11, HCDR2 having a sequence set forth in SEO ID NO: 12, and HCDR3 having a sequence set forth in SEO ID NO: 13; and a light chain variable region (VL) comprising the following 3 complementarity determining regions (CDRs): LCDR1 having a sequence set forth in SEO ID NO: 14, LCDR2 having a sequence set forth in SEO ID NO: 15, and LCDR3 having a sequence set forth in SEO ID NO: 16; or, (ii) an antibody or antigen-binding fragment thereof, which comprises: a heavy chain variable region (VH) comprising 3 CDRs contained in the VH set forth in SEO ID NO: 9; and a light chain variable region (VL) comprising 3 CDRs contained in the VL set forth in SEO ID NO: 10; wherein the 3 CDRs contained in the VH and the 3 CDRs contained in the VL are defined by the Kabat, Chothia or IMGT numbering system; or, (iii) an antibody or antigen-binding fragment thereof, wherein the antibody is a monoclonal antibody produced by a hybridoma cell line 2A7 which is deposited in the China Center for Type Culture Collection (CCTCC) and has the deposit number of CCTCC NO. C2019302.

2. The method according to claim 1, wherein the second antibody bears a detectable label; or, the determining as described in step (3) comprises using a third antibody with a detectable label.

3. The method according to claim 1, wherein, in step (3), the determining is selected from enzyme immunoassay or chemiluminescence immunoassay.

4. The method according to claim 1, wherein the first antibody is coated on the surface of a solid carrier.

5. The method according to claim 1, wherein the sample is selected from the group consisting of whole blood, plasma and serum.

6. The method according to claim 1, wherein, prior to step (1), the method further comprises a step of treating the sample, wherein the treating comprises: mixing a lysing agent with the sample so as to lyse virus; and/or prior to step (2) and/or step (3), the method further comprises a washing step.

7. A monoclonal antibody or antigen-binding fragment thereof capable of specifically binding to HBcAg, wherein, (i) the monoclonal antibody or antigen-binding fragment thereof comprises: a heavy chain variable region (VH) comprising the following 3 complementarity determining regions (CDRs): HCDR1 having a sequence set forth in SEQ ID NO: 11, HCDR2 having a sequence set forth in SEQ ID NO: 12, and HCDR3 having a sequence set forth in SEQ ID NO: 13; and, a light chain variable region (VL) comprising the following 3 complementarity determining regions (CDRs): LCDR1 having a sequence set forth in SEQ ID NO: 14, LCDR2 having a sequence set forth in SEQ ID NO: 15, and LCDR3 having a sequence set forth in SEQ ID NO: 16; or, (ii) an antibody or antigen-binding fragment thereof, which comprises: a heavy chain variable region (VH) comprising 3 CDRs contained in a heavy chain variable region set forth in SEQ ID NO: 9; and, a light chain variable region (VL) comprising 3 CDRs contained in a light chain variable region set forth in SEQ ID NO: 10; wherein the 3 CDRs contained in the heavy chain variable region, and/or the 3 CDRs contained in the light chain variable region are defined by the Kabat, Chothia or IMGT numbering system; or, (iii) an antibody or antigen-binding fragment thereof, wherein the antibody is a monoclonal antibody produced by a hybridoma cell line 2A7 which is deposited in the China Center for Type Culture Collection (CCTCC) and has the deposit number of CCTCC NO. C2019302.

8. The monoclonal antibody or antigen-binding fragment thereof according to claim 7, wherein the monoclonal antibody or antigen-binding fragment thereof comprises: a heavy chain variable region (VH) having the sequence set forth in SEQ ID NO: 9 or a sequence having a sequence identity of at least 80% compared thereto and the VH comprises HCDR1-HCDR3 set forth in SEQ ID NO: 11-13, respectively; and a light chain variable region (VL) having the sequence set forth in SEQ ID NO: 10 or a sequence having a sequence identity of at least 80% compared thereto and the VL comprises LCDR1-LCDR3 set forth in SEQ ID NO: 14-16, respectively.

9. The monoclonal antibody or antigen-binding fragment thereof according to claim 7, wherein the monoclonal antibody comprises a heavy chain constant region (CH) and a light chain constant region (CL).

10. A method for detection of HBcAg in a sample, wherein the detection is an immunological detection using the monoclonal antibody or antigen-binding fragment thereof according to claim 7 as the detection reagent.

11. The monoclonal antibody or antigen-binding fragment thereof according to claim 7, which is characterized by one or more of the following:

(i) the monoclonal antibody is an IgG, IgM, IgE, IgD or IgA antibody;

(ii) the antigen-binding fragment is selected from the group consisting of Fab, Fab', (Fab')$_2$, Fv, disulfide-linked Fv, scFv, diabody and single domain antibody (sdAb);

(iii) the monoclonal antibody is a murine antibody, a chimeric antibody or a humanized antibody.

12. The method according to claim 10, which is characterized by one or more of the following:

(i) the sample is a tissue sample or a cell sample;

(ii) the immunological detection is selected from immunohistochemistry (IHC), immunocytochemistry (ICC), immunofluorescence (IF) and Western Blot;

(iii) the detection reagent is the monoclonal antibody or the antigen-binding fragment thereof bearing a detectable label, or is the monoclonal antibody or the antigen-binding fragment thereof and a secondary antibody bearing a detectable label.

13. The method according to claim 1, wherein the first antibody is selected from an antibody or an antigen-binding fragment thereof, which comprises a heavy chain variable region (VH) and a light chain variable region (VL), wherein the VH comprises HCDR1-HCDR3 set forth in SEQ ID NO: 1-3, respectively and has the sequence set forth in SEQ ID NO: 1 or a sequence having a sequence identity of at least 80% compared thereto; and the VL comprises LCDR1-LCDR3 set forth in SEQ ID NO: 6-8, respectively and has the sequence set forth in SEQ ID NO: 2 or a sequence having a sequence identity of at least 80% compared thereto.

14. The method according to claim 1, wherein the second antibody is selected from an antibody or an antigen-binding fragment thereof, which comprises a heavy chain variable region (VH) and a light chain variable region (VL), wherein the VH comprises HCDR1-HCDR3 set forth in SEQ ID NO: 11-13, respectively and has the sequence set forth in SEQ ID NO: 9 or a sequence having a sequence identity of at least 80% compared thereto; and the VL comprises LCDR1-LCDR3 set forth in SEQ ID NO: 14-16, respectively and has the sequence set forth in SEQ ID NO: 10 or a sequence having a sequence identity of at least 80% compared thereto.

15. The method according to claim 1, wherein the first antibody and/or the second antibody comprises a heavy chain constant region (CH) and a light chain constant region (CL).

16. The method according to claim 1, wherein the first antibody and/or the second antibody is an IgG, IgM, IgE, IgD or IgA antibody.

17. The method according to claim 1, wherein the antigen-binding fragment is selected from the group consisting of Fab, Fab', (Fab')$_2$, Fv, disulfide-linked Fv, scFv, diabody and single domain antibody (sdAb); and/or, the antibody is a murine antibody, a chimeric antibody or a humanized antibody.

18. The method according to claim 2, wherein the detectable label is selected from enzyme, chemiluminescent reagent, fluorescent dye or biotin.

19. The method according to claim 4, wherein the solid carrier is selected from magnetic bead or microtiter plate.

* * * * *